(12) United States Patent
Bakker et al.

(10) Patent No.: US 9,907,955 B2
(45) Date of Patent: Mar. 6, 2018

(54) DISTURBING MAGNETIC RESONANCE IMAGING (MRI) IMAGES USING IMPLANTABLE MEDICAL DEVICE

(71) Applicant: Medtronic Bakken Research Center B.V., Maastricht (NL)

(72) Inventors: Jurriaan Bakker, Heeze (NL); Egbertus Johannes Maria Bakker, Wijk en aalburg (NL); Jeroen Jacob Arnold Tol, Eindhoven (NL); Marini Witjes, Gendt (NL)

(73) Assignee: Medtronic Bakken Research Center B.V., Maastricht (NL)

( * ) Notice: Subject to any disclaimer, the term of this patent is extended or adjusted under 35 U.S.C. 154(b) by 0 days.

(21) Appl. No.: 14/945,088

(22) Filed: Nov. 18, 2015

(65) Prior Publication Data

US 2016/0144167 A1    May 26, 2016

Related U.S. Application Data

(60) Provisional application No. 62/084,328, filed on Nov. 25, 2014.

(51) Int. Cl.

| *A61N 1/00* | (2006.01) |
|---|---|
| *A61N 1/08* | (2006.01) |
| *A61B 5/055* | (2006.01) |
| *A61N 1/37* | (2006.01) |
| *A61B 5/06* | (2006.01) |
| *G01R 33/28* | (2006.01) |
| *A61B 90/00* | (2016.01) |
| *A61B 5/00* | (2006.01) |

(52) U.S. Cl.
CPC ................ *A61N 1/08* (2013.01); *A61B 5/055* (2013.01); *A61B 5/06* (2013.01); *A61N 1/3718* (2013.01); *G01R 33/288* (2013.01); *A61B 5/0042* (2013.01); *A61B 5/0044* (2013.01); *A61B 2090/374* (2016.02); *A61B 2560/0276* (2013.01); *G01R 33/285* (2013.01)

(58) Field of Classification Search
CPC .................................. A61N 1/08; A61B 5/055
USPC ........................................................... 607/60
See application file for complete search history.

(56) References Cited

U.S. PATENT DOCUMENTS

| 7,509,167 B2 | 3/2009 | Stressman |
|---|---|---|
| 7,561,915 B1 | 7/2009 | Cooke et al. |
| 7,693,568 B2 | 4/2010 | Zeijlemaker |
| 8,583,210 B2 | 11/2013 | Doerr et al. |

(Continued)

FOREIGN PATENT DOCUMENTS

EP    2674193 A1    12/2013

OTHER PUBLICATIONS

International Preliminary Report on Patentability from International Application No. PCT/EP2015/077672, dated May 30, 2017, 6 pp.

(Continued)

*Primary Examiner* — Nadia A Mahmood
(74) *Attorney, Agent, or Firm* — Shumaker & Sieffert, P.A.

(57) ABSTRACT

In one example, a method includes delivering, via one or more stimulation generators of a medical device implanted in a patient, electrical stimulation to the patient. In this example, the method also includes disturbing, by one or more components of the medical device, an image of the patient generated by a magnetic resonance image (MRI) scanner.

14 Claims, 12 Drawing Sheets

(56) References Cited

U.S. PATENT DOCUMENTS

| | | | |
|---|---|---|---|
| 2005/0070975 A1 | 3/2005 | Zeijlemaker et al. | |
| 2007/0238975 A1* | 10/2007 | Zeijlemaker | A61N 1/3718 600/411 |
| 2007/0265685 A1 | 11/2007 | Zeijlemaker | |
| 2011/0106204 A1 | 5/2011 | Yoon et al. | |
| 2011/0148400 A1 | 6/2011 | Doerr et al. | |
| 2012/0109260 A1* | 5/2012 | Stancer | A61N 1/3718 607/60 |
| 2012/0169336 A1 | 7/2012 | Leigh et al. | |

OTHER PUBLICATIONS

International Search Report and Written Opinion of International Application No. PCT/EP2015/077672, dated Feb. 15, 2016, 9 pp.

* cited by examiner

DISTURBING MAGNETIC RESONANCE IMAGING (MRI) IMAGES USING IMPLANTABLE MEDICAL DEVICE

This application claims the benefit of U.S. Provisional Application No. 62/084,328, filed Nov. 25, 2014, the entire content of which is incorporated herein by reference.

TECHNICAL FIELD

The present disclosure relates implantable medical devices.

BACKGROUND

Implantable medical devices, such as electrical stimulators or therapeutic agent delivery devices, have been proposed for use in different therapeutic applications, such as deep brain stimulation (DBS), spinal cord stimulation (SCS), pelvic stimulation, gastric stimulation, peripheral nerve stimulation, functional electrical stimulation or delivery of pharmaceutical agents, insulin, pain relieving agents or anti-inflammatory agents to a target tissue site within a patient. In some therapy systems, an implantable electrical stimulator delivers electrical therapy to a target tissue site within a patient with the aid of one or more electrodes, which may be deployed by medical leads carrying elongated conductors, or on a housing of the electrical stimulator, or both.

Magnetic resonance imaging (MRI) is commonly used as a medical imaging technique used in radiology to investigate the anatomy and function of neurostructures such as the brain or the spinal cord or the like. MRI scanners use strong magnetic fields and radio waves to generate images of the patient's body.

However, patients with implantable medical devices such as neurostimulation and/or neurorecording devices might face some limitations during MRI, since the magnetic fields of the MRI scanner or the RF signals of the MRI might provide electromagnetic interferences (EMI) that may impact the function of the implantable medical device and/or lead to heating.

SUMMARY

In general, this disclosure is directed to an implantable medical device (IMD) configured to deliver electrical stimulation to a patient and to disturb images of the patient generated by MRI scanners. For example, when the patient in which the IMD is implanted is scanned by an MRI scanner, the IMD may emit one or more magnetic fields to disturb the image generated by the MRI scanner. An operator of the MRI scanner may notice that the generated images are disturbed, possibly interpreting the disturbance as an indication of the presence of the IMD within the patient, and perform one or more actions to avoid damaging the medical device and/or injuring the patient.

In one example, a method includes delivering, via one or more stimulation generators of an implantable medical device implanted in a patient, electrical stimulation to the patient; and disturbing, by one or more components of the medical device, an image of the patient generated by an MRI scanner.

In another example, an implantable medical device (IMD) includes one or more stimulation generators configured to generate electrical stimulation for delivery to a patient; and one or more components configured to disturb an image of the patient generated by an MRI scanner.

In another example, a computer-readable storage medium stores instructions that, when executed, cause one or more processors of an IMD to: cause one or more stimulation generators of the IMD to deliver electrical stimulation to a patient; and cause one or more components of the IMD to disturb an image of the patient generated by an MRI scanner.

In another example, an IMD includes: means for delivering electrical stimulation to a patient; and means for disturbing an image of the patient generated by an MRI scanner.

In another example, a method includes determining, based on aspects of magnetic fields detected by a magnetic field detector, whether a patient has an IMD configured to disturb images generated by an MRI scanner; and outputting an indication where the IMD is present.

In another example, a medical device detector includes a magnetic field detector; and one or more processors configured to: determine, based on aspects of magnetic fields detected by the magnetic field detector, whether a patient has an IMD configured to disturb images generated by an MRI scanner, and output an indication where the IMD is present.

In another example, a computer-readable storage medium stores instructions that, when executed, cause one or more processors of a medical device detector to: determine, based on aspects of magnetic fields detected by a magnetic field detector of the medical device detector, whether a patient has an IMD configured to disturb images generated by an MRI scanner; and output an indication where the IMD is present.

In another example, a medical device detector includes means for determining, based on aspects of magnetic fields detected by a magnetic field detector, whether a patient has an IMD configured to disturb images generated by an MRI scanner; and means for outputting an indication where the IMD is present.

The details of one or more examples are set forth in the accompanying drawings and the description below. Other features, objects, and advantages will be apparent from the description and drawings, and from the claims.

DETAILED DESCRIPTION

In some cases, an operator of an MRI scanner may not be aware that they are scanning or are about to scan a patient in which an implantable medical device (IMD) is implanted. As such, there is a possibility that the magnetic fields of the MRI scanner or the RF signals of the MRI might provide electromagnetic interferences (EMI) that may impact the function of the IMD and/or lead to heating. In some cases, such as where the operator is aware that a patient has an IMD but believes the patent may still be scanned within certain limits (e.g., where the patient has an MRI conditional IMD), the operator may not be aware of the limits of the IMD. As such, there is a possibility that the patient is scanned at parameters that exceed the limits of the device (e.g., manufacturer's recommended limits).

In accordance with one or more techniques of this disclosure, an IMD may be configured to disturb images generated by an MRI scanner. The IMD may disturb the images by causing visible artifacts to appear in the images by the MRI scanner. For example, the IMD may cause zipper artifacts, hatching artifacts, strike-throughs, or the like to appear in the images generated by the MRI scanner and presented to a user on a display. In some examples, the MRI operator (clinician, physician) may view the artifacts in the images generated by the MRI scanner. In some examples, an image processor coupled to the MRI scanner may detect the artifacts in the images and output an alert to the MRI operator. In either of these ways, the MRI operator may be alerted (i.e., by the disturbed MR image or the alert) that the patient has an IMD and/or that the MRI scanner has exceeded the limits of the IMD.

Figure 1:
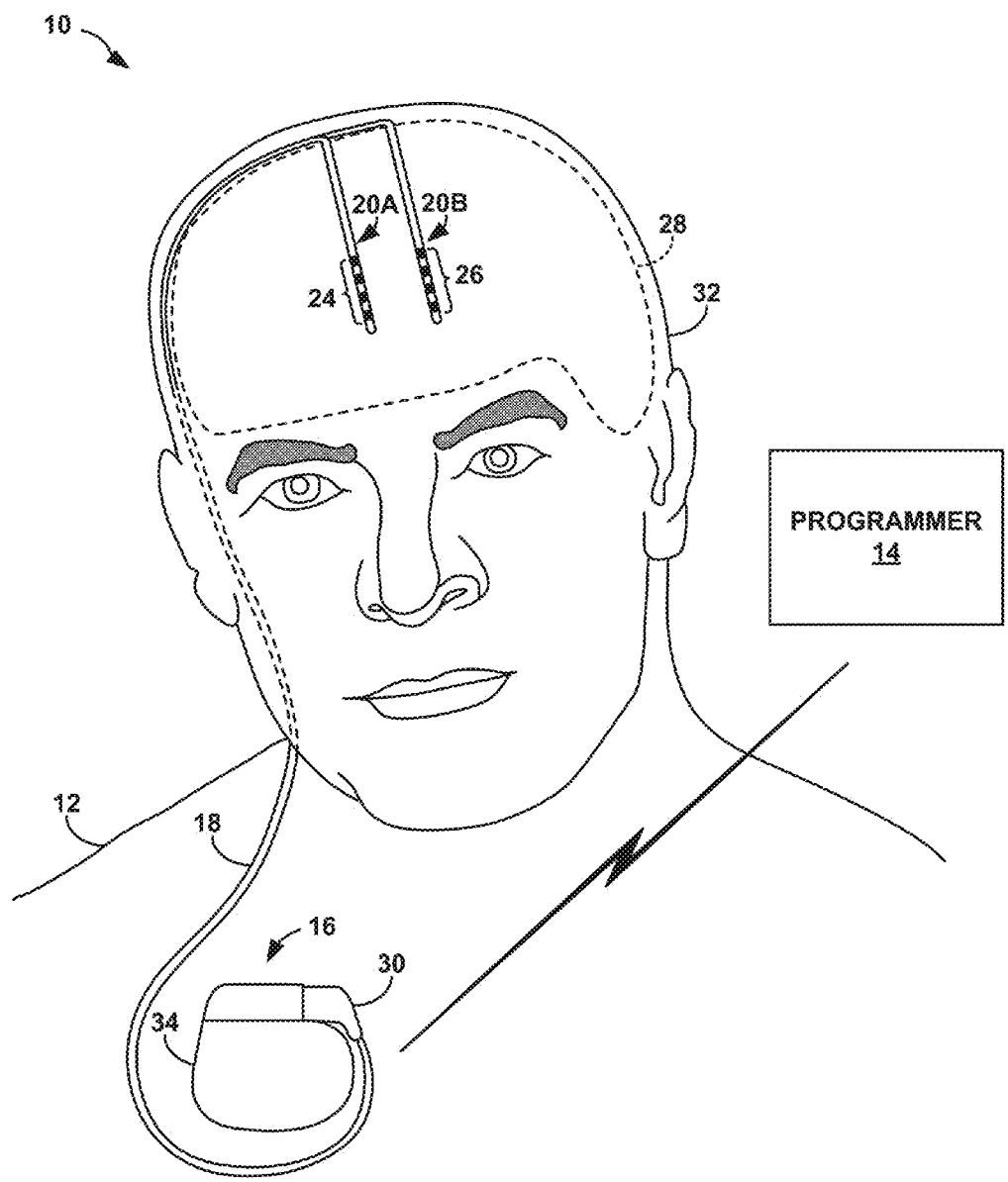
FIG. 1 is a conceptual diagram illustrating an example therapy system 10 that is configured to deliver therapy to a patient to manage a disorder of the patient, in accordance with one or more techniques of the disclosure.

FIG. 1 is a conceptual diagram illustrating an example therapy system 10 that is configured to deliver therapy to patient 12 to manage a disorder of patient 12, in accordance with one or more techniques of the disclosure. Patient 12 ordinarily will be a human patient. In some cases, however, therapy system 10 may be applied to other mammalian or non-mammalian non-human patients. In the example shown in FIG. 1, therapy system 10 includes medical device programmer 14, implantable medical device (IMD) 16, lead extension 18, and one or more leads 20A and 20B (collectively "leads 20") with respective sets of electrodes 24, 26. IMD 16 includes a stimulation generator configured to generate and deliver electrical stimulation therapy to one or more regions of brain 28 of patient 12 via one or more electrodes 24, 26 of leads 20A and 20B, respectively.

In the example shown in FIG. 1, therapy system 10 may be referred to as a deep brain stimulation (DBS) system because IMD 16 is configured to deliver electrical stimulation therapy directly to tissue within brain 28, e.g., a tissue site under the dura mater of brain 28 or one or more branches or nodes, or a confluence of fiber tracks. In other examples, leads 20 may be positioned to deliver therapy to a surface of brain 28 (e.g., the cortical surface of brain 28). For example, in some examples, IMD 16 may provide cortical stimulation therapy to patient 12, e.g., by delivering electrical stimulation to one or more tissue sites in the cortex of brain 28. As another example, IMD 16 may provide vagal nerve stimulation (VNS) therapy to patient 12 by delivering electrical stimulation to one or more vagal nerve tissue sites.

DBS may be used to treat or manage various patient conditions, such as, but not limited to, seizure disorders (e.g., epilepsy), pain, migraine headaches, psychiatric disorders (e.g., major depressive disorder (MDD), bipolar disorder, anxiety disorders, post-traumatic stress disorder, dysthymic disorder, and obsessive compulsive disorder (OCD)), behavior disorders, mood disorders, memory disorders, mentation disorders, movement disorders (e.g., essential tremor or Parkinson's disease), Huntington's disease, Alzheimer's disease, or other neurological or psychiatric disorders and impairment of patient 12.

Therapy systems configured for treatment of other patient conditions via delivery of therapy to brain 28 or another suitable target therapy delivery site in patient 12 can also be used in accordance with the techniques disclosed herein. For example, in other applications of therapy system 10, the target therapy delivery site within patient 12 may be a location proximate to a spinal cord or sacral nerves (e.g., the S2, S3 or S4 sacral nerves) in patient 12 or any other suitable nerve, organ, muscle or muscle group in patient 12, which may be selected based on, for example, a patient condition.

For example, therapy system 10 may be used to deliver electrical stimulation or a therapeutic agent to tissue proximate to a pudendal nerve, a perineal nerve or other areas of the nervous system, in which cases, leads 20 would be implanted and substantially fixed proximate to the respective nerve. As further examples, an electrical stimulation system may be positioned to deliver a stimulation to help manage peripheral neuropathy or post-operative pain mitigation, ilioinguinal nerve stimulation, intercostal nerve stimulation, gastric stimulation for the treatment of gastric mobility disorders and obesity, urinary dysfunction, fecal dysfunction, sexual dysfunction, muscle stimulation, for mitigation of other peripheral and localized pain (e.g., leg pain or back pain).

In the example shown in FIG. 1, IMD 16 may be implanted within a subcutaneous pocket in the pectoral region of patient 12. In other examples, IMD 16 may be implanted within other regions of patient 12, such as a subcutaneous pocket in the abdomen or buttocks of patient 12 or proximate the cranium of patient 12. Implanted lead extension 18 is coupled to IMD 16 via connector block 30 (also referred to as a header), which may include, for example, electrical contacts that electrically couple to respective electrical contacts on lead extension 18. The electrical contacts electrically couple the electrodes 24, 26 carried by leads 20 to IMD 16. Lead extension 18 traverses from the implant site of IMD 16 within a chest cavity of patient 12, along the neck of patient 12 and through the cranium of patient 12 to access brain 28. IMD 16 can be constructed of a biocompatible material that resists corrosion and degradation from bodily fluids. IMD 16 may comprise a hermetically sealed housing 34 to substantially enclose components, such as a processor, a therapy module, and memory.

In the example shown in FIG. 1, leads 20 are implanted within the right and left hemispheres, respectively, of brain 28 in order to deliver electrical stimulation to one or more regions of brain 28, which may be selected based on many factors, such as the type of patient condition for which therapy system 10 is implemented to manage. Other implant sites for leads 20 and IMD 16 are contemplated. For example, IMD 16 may be implanted on or within cranium 32 or leads 20 may be implanted within the same hemisphere at multiple target tissue sites or IMD 16 may be coupled to a single lead that is implanted in one or both hemispheres of brain 28.

Leads 20 may be positioned to deliver electrical stimulation to one or more target tissue sites within brain 28 to manage patient symptoms associated with a disorder of patient 12. Leads 20 may be implanted to position electrodes 24, 26 at desired locations of brain 28 via any suitable technique, such as through respective burr holes in the skull of patient 12 or through a common burr hole in the cranium 32. Leads 20 may be placed at any location within brain 28 such that electrodes 24, 26 are capable of providing electrical stimulation to target therapy delivery sites within brain 28 during treatment.

Different neurological or psychiatric disorders may be associated with activity in one or more of regions of brain 28, which may differ between patients. Accordingly, the target therapy delivery site for electrical stimulation therapy delivered by leads 20 may be selected based on the patient condition. For example, a suitable target therapy delivery site within brain 28 for controlling a movement disorder of patient 12 may include one or more of the pedunculopontine nucleus (PPN), thalamus, basal ganglia structures (e.g., globus pallidus, substantia nigra or subthalamic nucleus), zona inserta, fiber tracts, lenticular fasciculus (and branches thereof), ansa lenticularis, or the Field of Forel (thalamic fasciculus). The PPN may also be referred to as the pedunculopontine tegmental nucleus.

As another example, in the case of MDD, bipolar disorder, OCD, or other anxiety disorders, leads 20 may be implanted to deliver electrical stimulation to the anterior limb of the internal capsule of brain 28, and only the ventral portion of the anterior limb of the internal capsule (also referred to as a VC/VS), the subgenual component of the cingulate cortex (which may be referred to as CG25), anterior cingulate cortex Brodmann areas 32 and 24, various parts of the prefrontal cortex, including the dorsal lateral and medial pre-frontal cortex (PFC) (e.g., Brodmann area 9), ventromedial prefrontal cortex (e.g., Brodmann area 10), the lateral and medial orbitofrontal cortex (e.g., Brodmann area 11), the medial or nucleus accumbens, thalamus, intralaminar thalamic nuclei, amygdala, hippocampus, the lateral hypothalamus, the Locus ceruleus, the dorsal raphe nucleus, ventral tegmentum, the substantia nigra, subthalamic nucleus, the inferior thalamic peduncle, the dorsal medial nucleus of the thalamus, the habenula, the bed nucleus of the stria terminalis, or any combination thereof.

As another example, in the case of a seizure disorder or Alzheimer's disease, for example, leads 20 may be implanted to deliver electrical stimulation to regions within the Circuit of Papez, such as, e.g., one or more of the anterior thalamic nucleus, the internal capsule, the cingulate, the fornix, the mammillary bodies, the mammillothalamic tract (mammillothalamic fasciculus), or the hippocampus.

As another example, in the case of Parkinson's disease, for example, leads 20 may be implanted to deliver electrical stimulation to regions within the subthalamic nucleus (STN), either unilaterally or bilaterally. Target therapy delivery sites not located in brain 28 of patient 12 are also contemplated.

Although leads 20 are shown in FIG. 1 as being coupled to a common lead extension 18, in other examples, leads 20 may be coupled to IMD 16 via separate lead extensions or directly coupled to IMD 16. Moreover, although FIG. 1 illustrates system 10 as including two leads 20A and 20B coupled to IMD 16 via lead extension 18, in some examples, system 10 may include one lead or more than two leads.

In the examples shown in FIG. 1, electrodes 24, 26 of leads 20 are shown as ring electrodes. Ring electrodes may be relatively easy to program and may be capable of delivering an electrical field to any tissue adjacent to leads 20. In other examples, electrodes 24, 26 of leads 20 may have different configurations. For example, one or more of the electrodes 24, 26 of leads 20 may have a complex electrode array geometry that is capable of producing shaped electrical fields, including interleaved stimulation.

An example of a complex electrode array geometry may include an array of electrodes positioned at different axial positions along the length of a lead, as well as at different angular positions about the periphery, e.g., circumference, of the lead. The complex electrode array geometry may include multiple electrodes (e.g., partial ring electrodes or segmented electrodes) around the perimeter of each lead 20, in addition to, or instead of, a ring electrode. In some examples, the electrodes are made using thin film techniques.

In this manner, electrical stimulation may be directed to a specific direction from leads 20 to enhance therapy efficacy and reduce possible adverse side effects from stimulating a large volume of tissue. As a further example, the electrodes may be pad electrodes, which may be carried on a paddle lead or a cylindrical lead.

In some examples, outer housing 34 of IMD 16 may include one or more stimulation and/or sensing electrodes. For example, housing 34 can comprise an electrically conductive material that is exposed to tissue of patient 12 when IMD 16 is implanted in patient 12, or an electrode can be attached to housing 34. In other examples, leads 20 may have shapes other than elongated cylinders as shown in FIG. 1 with active or passive tip configurations. For example, leads 20 may be paddle leads, spherical leads, bendable leads, or any other type of shape effective in treating patient 12.

IMD 16 may deliver electrical stimulation therapy to brain 28 of patient 12 according to one or more stimulation therapy programs (also referred to herein as "set of stimulation parameter values"). A stimulation therapy program may define one or more electrical stimulation parameter values for therapy generated by a stimulation generator of IMD 16 and delivered from IMD 16 to a target therapy delivery site within patient 12 via one or more electrodes 24, 26.

The electrical stimulation parameters may define an aspect of the electrical stimulation therapy, and may include, for example, voltage or current amplitude of an electrical stimulation signal, a frequency of the electrical stimulation signal, waveform shape, on/off cycling state (e.g., if cycling is "off," stimulation is always on, and if cycling is "on," stimulation is cycled on and off) and, in the case of electrical stimulation pulses, pulse rate, pulse width, and other appropriate parameters such as duration or duty cycle. In addition, if different electrodes are available for delivery of stimulation, a therapy parameter of a therapy program may be further characterized by an electrode combination, which may define selected electrodes 24, 26 and their respective polarities. In some examples, stimulation may be delivered using a continuous waveform and the stimulation parameters may define this waveform.

In addition to being configured to deliver therapy to manage a disorder of patient 12, therapy system 10 may be configured to sense bioelectrical brain signals or another physiological parameter of patient 12. For example, IMD 16 may include a sensing module that is configured to sense bioelectrical brain signals within one or more regions of brain 28 via a subset of electrodes 24, 26, another set of electrodes, or both. Accordingly, in some examples, electrodes 24, 26 may be used to deliver electrical stimulation from the therapy module to target sites within brain 28 as well as sense brain signals within brain 28. However, IMD 16 can also use a separate set of sensing electrodes to sense the bioelectrical brain signals. In some examples, the sensing module of IMD 16 may sense bioelectrical brain signals via one or more of the electrodes 24, 26 that are also used to deliver electrical stimulation to brain 28. In other examples, one or more of electrodes 24, 26 may be used to sense bioelectrical brain signals while one or more different electrodes 24, 26 may be used to deliver electrical stimulation.

External medical device programmer 14 is configured to wirelessly communicate with IMD 16 as needed to provide or retrieve therapy information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. In addition, or instead, programmer 14 may be a patient programmer that allows patient 12 to select programs and/or view and modify therapy parameter values. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device, voice activation, or another input mechanism that allows the user to navigate through the user interface of programmer 14 and provide input. If programmer 14 includes buttons and a keypad, the buttons may be dedicated to performing a certain function, e.g., a power button, the buttons and the keypad may be soft keys that change in function depending upon the section of the user interface currently viewed by the user, or any combination thereof.

In other examples, programmer 14 may be a larger workstation or a separate application within another multi-function device, rather than a dedicated computing device. For example, the multi-function device may be a notebook computer, tablet computer, workstation, one or more servers, cellular phone, personal digital assistant, or another computing device that may run an application that enables the computing device to operate as a secure medical device programmer 14. A wireless adapter coupled to the computing device may enable secure communication between the computing device and IMD 16.

When programmer 14 is configured for use by the clinician, programmer 14 may be used to transmit programming information to IMD 16. Programming information may include, for example, hardware information, such as the type of leads 20, the arrangement of electrodes 24, 26 on leads 20, the position of leads 20 within brain 28, one or more therapy programs defining therapy parameter values, therapeutic windows for one or more electrodes 24, 26, and any other information that may be useful for programming into IMD 16. Programmer 14 may also be capable of completing functional tests (e.g., measuring the impedance of electrodes 24, 26 of leads 20).

The clinician may also generate and store therapy programs within IMD 16 with the aid of programmer 14. Programmer 14 may assist the clinician in the creation/identification of therapy programs by providing a system for identifying potentially beneficial therapy parameter values. In some examples, at least some of the therapy programs may have the same electrode combination (but different values of at least one other therapy parameter) and these therapy programs may be organized into subsets, each subset having the same electrode combination. A processor of programmer 14 may select the most efficacious therapy program for each subset and display a list of the selected therapy programs. The clinician may select a therapy program from the list to provide therapy to patient 12 to address symptoms associated with the patient condition.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12.

Whether programmer 14 is configured for clinician or patient use, programmer 14 is configured to communicate with IMD 16 and, optionally, another computing device, via wireless communication. Programmer 14, for example, may communicate via wireless communication with IMD 16 using RF and/or inductive telemetry techniques known in the art, which may comprise techniques for proximal, mid-range, or longer-range communication.

Programmer 14 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols.

Programmer 14 may also communicate with other programming or computing devices via exchange of removable media, such as magnetic or optical disks, memory cards, or memory sticks. Further, programmer 14 may communicate with IMD 16 and another programmer via remote telemetry techniques known in the art, communicating via a personal area network (PAN), a local area network (LAN), wide area network (WAN), public switched telephone network (PSTN), or cellular telephone network, for example.

Therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment.

While DBS may successfully reduce symptoms of some neurological diseases, the stimulation may also cause unwanted side effects, also referred to herein as adverse effects. Side effects may include incontinence, tingling, loss of balance, paralysis, slurred speech, loss of memory, loss of inhibition, and many other neurological problems. Side effects may be mild to severe. DBS may cause one or more adverse effects by inadvertently providing electrical stimulation pulses to anatomical regions near the targeted anatomical region. These anatomical regions may be referred to as regions associated with adverse stimulation effects. For this reason, a clinician may program IMD 16 with a therapy program (or a plurality of therapy programs) that defines stimulation parameter values that balance effective therapy and minimize side effects.

With the aid of programmer 14 or another computing device, a clinician may select values for therapy parameters for therapy system 10, including an electrode combination. By selecting particular electrodes 24, 26 for delivering electrical stimulation therapy to patient 12, a clinician may modify the electrical stimulation therapy to target one or more particular regions of tissue (e.g., specific anatomical structures) within brain 28 and avoid other regions of tissue within brain 28. In addition, by selecting values for the other stimulation parameter values that define the electrical stimulation signal, e.g., the electrical voltage or current amplitude, pulse width, and pulse rate, the clinician may generate an efficacious therapy for patient 12 that is delivered via the selected electrode subset. Due to physiological diversity, condition differences, and inaccuracies in lead placement, the parameter values may vary between patients.

During a programming session, the clinician may determine one or more therapy programs that may provide effective therapy to patient 12. Patient 12 may provide feedback to the clinician as to the efficacy of the specific program being evaluated, which may include information regarding adverse effects of delivery of therapy according to the specific program. In some examples, the patient feedback may be used to determine a clinical rating scale score. Once the clinician has identified one or more programs that may be beneficial to patient 12, patient 12 may continue the evaluation process and determine which program best alleviates the condition of patient 12 or otherwise provides efficacious therapy to patient 12. Programmer 14 may assist the clinician in the creation/identification of therapy programs by providing a methodical system of identifying potentially beneficial therapy parameters.

In accordance with one or more techniques of this disclosure, and as discussed in further detail below, in some examples, IMD 16 may be configured to disturb an image of patient 12 generated by an MRI scanner. To disturb the image, one or more components of IMD 16 may be configured to generate one or more magnetic fields.

As one example, a stimulation generator of IMD 16 may generate low frequency magnetic fields (e.g., magnetic fields in a frequency range of 0 Hertz to 5000 Hertz). By generating low frequency magnetic fields, IMD 16 may distort the local magnetic field gradients used by the MRI scanner for image localization. As another example, a radio frequency (RF) transmitter of IMD 16 (such as magnetic fields in an RF transmitter used by IMD 16 to communicate with programmer 14) may generate RF electromagnetic fields (e.g., in a frequency range of 30 Mega-Hertz to 5000 Mega-Hertz).

By generating RF electromagnetic fields, IMD 16 may distort the MRI scanner's read-out of the Larmor resonance frequencies of i.e. protons, which may lead to a large image intensity change. By providing sufficient bandwidth around the Larmor frequency, protons outside the region of interest (ROI) may be excited, which may lead to unwanted MR signal generation and disturbing of the image. In some examples, the images generated by an MRI scanner when IMD 16 is generating the one or more magnetic fields may be disturbed in a manner similar to the images of FIGS. 10A-10C. In this way, IMD 16 may disturb an image of patient 12 generated by an MRI scanner.

In some examples, IMD 16 may be configured to send identification information which can be identified by an MRI scanner. For instance, IMD 16 may include an RF identification tag, that can be picked up by RF receive coils of an MRI scanner, such that the MRI software or the MRI manufacturer has the possibility to get more detailed information of the cause of the image artifact (i.e. by sending the identification information, MR condition information, or the like). In this way, the MRI scanner may directly determine information about the IMD (e.g., that a general IMD is present, or the type of the IMD).

In some examples, devices other than MRI scanners may be used to detect the presence/existence of an IMD. As one example, a hand-held detector may be used to screen a patient prior to entering an MRI scanner. For instance, a hand-held detector could be operable to determine that an IMD is attempting to disturb an image generated by an MRI scanner. Further details of such a detector are discussed below with reference to FIG. 7.

Figure 2:
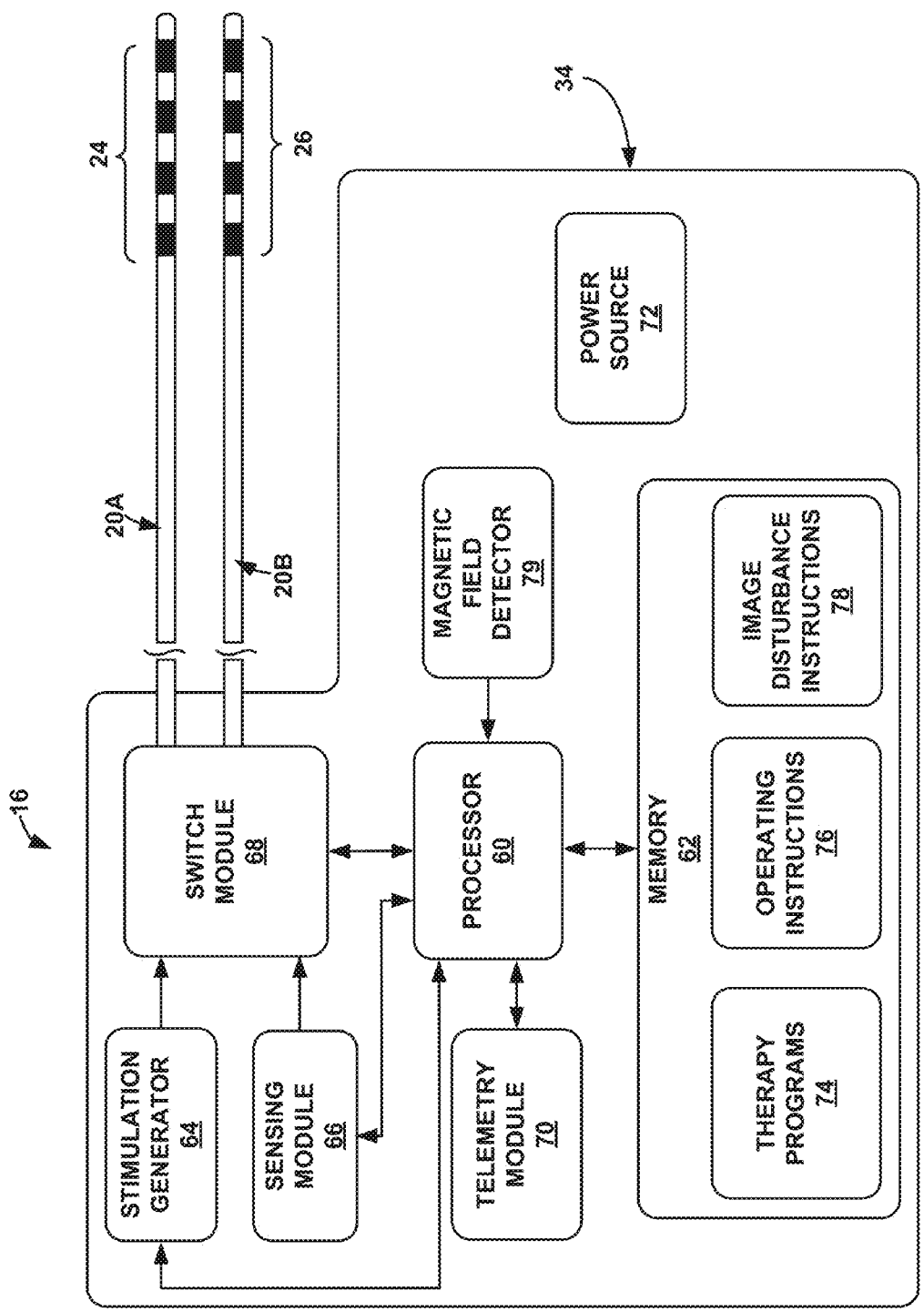
FIG. 2 is functional block diagram illustrating components of an example IMD, in accordance with one or more techniques of the disclosure.

FIG. 2 is functional block diagram illustrating components of an example IMD 16. In the example shown in FIG. 2, IMD 16 includes processor 60, memory 62, stimulation generator 64, sensing module 66, switch module 68, telemetry module 70, power source 72, and magnetic field detector 79. Memory 62, as well as other memories described herein, may include any volatile or non-volatile media, such as a random access memory (RAM), read only memory (ROM), non-volatile RAM (NVRAM), electrically erasable programmable ROM (EEPROM), flash memory, and the like. Memory 62 may store computer-readable instructions that, when executed by processor 60, cause IMD 16 to perform various functions described herein.

In the example shown in FIG. 2, memory 62 may store therapy programs 74, operating instructions 76, and image disturbance instructions 78, e.g., in separate memories within memory 62 or separate areas within memory 62. Each stored therapy program 74 defines a particular program of therapy in terms of respective values for electrical stimulation parameters, such as an electrode combination, current or voltage amplitude, and, if stimulation generator 64 generates and delivers stimulation pulses, the therapy programs may define values for a pulse width, and pulse rate of a stimulation signal. Each stored therapy program 74 may also be referred to as a set of stimulation parameter values. Operating instructions 76 guide general operation of IMD 16 under control of processor 60, and may include instructions for monitoring brain signals within one or more brain regions via electrodes 24, 26 and delivering electrical stimulation therapy to patient 12.

Stimulation generator 64, under the control of processor 60, generates stimulation signals for delivery to patient 12 via selected combinations of electrodes 24, 26. In some examples, stimulation generator 64 generates and delivers stimulation signals to one or more target regions of brain 28 (FIG. 1), via a selected combination of electrodes 24, 26, based on one or more stored therapy programs 74. The target tissue sites within brain 28 for stimulation signals or other types of therapy and stimulation parameter values may depend on the patient condition for which therapy system 10 is implemented to manage. While stimulation pulses are described, stimulation signals may be of any form, such as continuous-time signals (e.g., sine waves) or the like.

The processors described in this disclosure, including processor 60, may include one or more digital signal processors (DSPs), general purpose microprocessors, application specific integrated circuits (ASICs), field programmable logic arrays (FPGAs), or other equivalent integrated or discrete logic circuitry, or combinations thereof. The functions attributed to processors described herein may be provided by a hardware device and embodied as software, firmware, hardware, or any combination thereof. Processor 60 is configured to control stimulation generator 64 according to therapy programs 74 stored by memory 62 to apply particular stimulation parameter values specified by one or more programs, such as amplitude, pulse width, and pulse rate.

Processor 60 may control switch module 68 to apply the stimulation signals generated by stimulation generator 64 to a selected combination of electrodes 24 and/or electrodes 26 (which, as discussed above, may have a complex geometry that is capable of producing shaped electrical fields, including interleaved stimulation). In particular, switch module 68 may couple stimulation signals to selected conductors within leads 20, which, in turn, deliver the stimulation signals across selected electrodes 24 and/or electrodes 26. Switch module 68 may be a switch array, switch matrix, multiplexer, or any other type of switching module configured to selectively couple stimulation energy to selected electrodes 24 and/or electrodes 26 and to selectively sense bioelectrical brain signals with selected electrodes 24 and/or electrodes 26. Hence, stimulation generator 64 is coupled to electrodes 24 and/or electrodes 26 via switch module 68 and conductors within leads 20. In some examples, however, IMD 16 does not include switch module 68. For instance, in some examples, IMD 16 may include individual voltage or current sources coupled to each electrode (i.e., a separate voltage and/or current source for each of electrodes 24 and/or electrodes 26).

As discussed above, processor 60 may control switch module 68 to apply the stimulation signals generated by stimulation generator 64 to a selected combination of electrodes 24 and/or electrodes 26. In some examples, the selected combination of electrodes 24 and/or electrodes 26 may be unipolar. For instance, a unipolar selected combination may include one electrode of either electrodes 24 or electrodes 26 in combination with an electrode on the housing of IMD 16 (i.e., case or can), where one is an anode and the other is a cathode. In some examples, the selected combination of electrodes 24 and/or electrodes 26 may be bipolar. As one example, a bipolar selected combination may include two electrodes from electrodes 24, where one is an anode and the other is a cathode. As another example, a bipolar selected combination may include two electrodes from electrodes 26, where one is an anode and the other is a cathode. As another example, a bipolar selected combination may include an electrode from electrodes 24 and an electrode from electrodes 26, where one is an anode and the other is a cathode. In some examples, the selected combination of electrodes 24 and/or electrodes 26 may be multipolar. As one example, a multipolar selected combination may include multiple anodes and/or multiple cathodes selected from electrodes 24. As another example, a multipolar selected combination may include multiple anodes and/or multiple cathodes selected from electrodes 26. As one example, a multipolar selected combination may include multiple anodes and/or multiple cathodes selected from electrodes 24 and electrodes 26.

Stimulation generator 64 may be a single channel or multi-channel stimulation generator. In particular, stimulation generator 64 may be capable of delivering a single stimulation pulse, multiple stimulation pulses or a continuous signal at a given time via a single electrode combination or multiple stimulation pulses at a given time via multiple electrode combinations. In some examples, however, stimulation generator 64 and switch module 68 may be configured to deliver multiple channels on a time-interleaved basis. For example, switch module 68 may serve to time divide the output of stimulation generator 64 across different electrode combinations at different times to deliver multiple programs or channels of stimulation energy to patient 12.

Sensing module 66, under the control of processor 60, is configured to sense bioelectrical brain signals of patient 12 via a selected subset of electrodes 24 and/or electrodes 26 or with one or more electrodes 24 and/or electrodes 26 and at least a portion of a conductive outer housing 34 of IMD 16, an electrode on an outer housing of IMD 16 or another reference. Processor 60 may control switch module 68 to electrically connect sensing module 66 to selected electrodes 24 and/or electrodes 26. In this way, sensing module 66 may selectively sense bioelectrical brain signals with different combinations of electrodes 24 and/or electrodes 26 (and/or a reference other than an electrode of electrodes 24 and/or electrodes 26).

Although sensing module 66 is incorporated into a common housing 34 with stimulation generator 64 and processor 60 in FIG. 2, in other examples, sensing module 66 is in a separate outer housing from outer housing 34 of IMD 16 and communicates with processor 60 via wired or wireless communication techniques.

Telemetry module 70 is configured to support wireless communication between IMD 16 and an external programmer 14 or another computing device under the control of processor 60. Processor 60 of IMD 16 may receive, as updates to programs, values for various stimulation parameters such as amplitude and electrode combination, from programmer 14 via telemetry module 70. The updates to the therapy programs may be stored within therapy programs 74 portion of memory 62. Telemetry module 70 in IMD 16, as well as telemetry modules in other devices and systems described herein, such as programmer 14, may accomplish communication by RF communication techniques. For instance, telemetry module 70 may include an RF antenna and an RF generator configured to generate RF electromagnetic fields via the RF antenna. In addition, telemetry module 70 may communicate with external medical device programmer 14 via proximal inductive interaction of IMD 16 with programmer 14. Accordingly, telemetry module 70 may send information to external programmer 14 on a continuous basis, at periodic intervals, or upon request from IMD 16 or programmer 14.

Power source 72 delivers operating power to various components of IMD 16. Power source 72 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Magnetic field detector 79 may detect the presence and/or intensity of a magnetic field. In some examples, magnetic field detector 79 may detect an MRI gradient magnetic field via inductive coupling of the field with one of three orthogonal coils, depending upon the orientation of the gradient magnetic field. In other examples, magnetic field detector 79 may be a linear magnetic field detector that is capable of detecting magnetic field gradients, and which also is capable of detecting magnetic field intensities. Magnetic field detector 79 provides an output indicating the intensity of the magnetic field to one or more components of IMD 16, such as processor 60. The output of magnetic field detector 79 may be a relatively unprocessed signal, or may be an indication of a relative intensity of the magnetic field, e.g., no magnetic field, low intensity magnetic field, or high intensity magnetic field.

In accordance with one or more techniques of this disclosure, in some examples, memory 62 may store image disturbance instructions 78, which may include instructions that are executable by processor 60 to cause one or more components of IMD 16 to disturb an image, such as an image generated by an MRI scanner of a patient in which IMD 16 is implanted. For instance, image disturbance instructions 78 may be executable by processor 60 to cause one or more components of IMD 16, such as a low frequency magnetic field generator and/or a RF electromagnetic field generator, to generate magnetic fields to disturb an image generated by an MRI scanner.

In some examples, processor 60 may re-purpose one or more components of IMD 16 to generate the magnetic fields to disturb images generated by MRI scanners. For instance, processors 60 may use one or both or stimulation generator 64 and telemetry module 70 to generate the magnetic fields to disturb images generated by MRI scanners. In other examples, processor 60 may use one or more disturb-specific components of IMD 16 to generate the magnetic fields to disturb images generated by MRI scanners.

In some examples, processor 60 may use stimulation generator 64 as the low frequency magnetic field generator. For instance, processor 60 may cause stimulation generator 64 to output electrical signals that create low frequency magnetic fields. In some of such examples, processor 60 may cause switch module 68 to refrain from coupling the electrical signals into electrodes 24. In some of such examples, processor 60 may cause switch module 68 to couple the electrical signals into one or more of electrodes 24. In this way, processor 60 may use components of IMD 16 that are already present to generate the low frequency magnetic fields. Furthermore, stimulation generator 64 may provide sufficient space to integrate the low frequency magnetic field generator into IMD 16. In some examples, stimulation generator 64 may be configured to generate the low frequency magnetic fields in parallel with the stimulation signals for delivery to patient 12, such that stimulation generator 64 may simultaneously generate both the low frequency magnetic fields and the stimulation signals for delivery to patient 12.

In some examples, stimulation generator 64 may not be configured to generate the low frequency magnetic fields in parallel with (i.e., at the same time as) the stimulation signals for delivery to patient 12, such that stimulation generator 64 may either generate the low frequency magnetic fields or the stimulation signals for delivery to patient 12. In other examples, stimulation generator 64 may be configured to generate the low frequency magnetic fields in parallel with (i.e., at the same time as) stimulation signals for delivery to patient 12. In some of such examples, by generating the stimulation signals for delivery to patient 12, stimulation generator 64 may generate the low frequency magnetic fields. In some examples, the stimulation generator 64 may time-interleave delivery of the stimulation signals with generation of the low frequency magnetic field.

In some examples, processor 60 may use an RF transmitter of telemetry module 70 as the RF electromagnetic field generator. For instance, processor 60 may cause an RF transmitter of telemetry module 70 to output, via an antenna, RF electromagnetic fields. As such an RF transmitter may already be present in IMD 16, processor 60 may cause RF electromagnetic fields to be generated without additional components. However, in some examples, slight modification e.g. in the software and/or the electronics layout of telemetry module 70 may be needed. In this way, processor 60 may control components of IMD 16 that may already be present, such as stimulation generator 64 or telemetry module 70, to generate the RF electromagnetic fields.

In some examples, image disturbance instructions 78, as executed by processor 60, may cause IMD 16 to operate in a plurality of modes, such as an MRI mode, a stimulation mode, and a disturb mode. In the disturb mode, image disturbance instructions 78 may cause one or more components of IMD 16 to emit an RF electromagnetic field to disturb an image as discussed above. In the stimulation mode, IMD 16 may deliver electrical stimulation to patient 12 (e.g., stimulation generator 64 may generate stimulation signals for delivery to brain 28 or heart 13 of patient 12, though other stimulation targets are possible). In the MRI mode, image disturbance instructions 78 may not cause one or more components of IMD 16 to disturb an image, but rather permit MRI images to be obtained without disturbance from the IMD. In some examples, IMD 16 may operate in more than one mode at a time. For instance, IMD 16 may operate in both the stimulation mode and the disturb mode at the same time.

In some examples, image disturbance instructions 78, as executed by processor 60, may cause IMD 16 to operate in the disturb mode on an on-demand basis, e.g., on demand by a user or in response to detection of an MRI field. For instance, image disturbance instructions 78 may cause IMD 16 to operate in the disturb mode in response to detecting a magnetic field, such as a magnetic field generated by an MRI scanner. Image disturbance instructions 78 may determine whether a magnetic field is detected based on a signal received from magnetic field detector 79. In some examples, image disturbance instructions 78 may determine that a magnetic field is present if the signal received from magnetic field detector 79 indicates that a high-intensity magnetic field, such as the magnetic field generated by an MRI scanner, is present.

In some examples, image disturbance instructions 78, as executed by processor 60, may determine that a magnetic field is present if the signal received from magnetic field detector 79 indicates that one or more aspects, such as the intensity, of a present magnetic field exceed one or more limits of IMD 16. In some examples, image disturbance instructions 78 may cause IMD 16 to operate in the disturb mode whenever not operating in the MRI mode. In other words, in some examples, image disturbance instructions 78 may cause IMD 16 to operate in the disturb mode regardless of whether a magnetic field is detected. As discussed above, when operating in the disturb mode, image disturbance instructions 78 may cause one or more components of IMD 16 to disturb images of patient 12 generated by an MRI scanner.

In some examples, image disturbance instructions 78, as executed by processor 60, may cause IMD 16 to operate in the MRI mode based on one or more requests received from external devices, such as programmer 14. For instance, image disturbance instructions 78 may cause IMD 16 to operate in the MRI mode in response to receiving a request from programmer 14 (e.g., via telemetry module 70) for IMD 16 to operate in the MRI mode. In some examples, image disturbance instructions 78 may cause IMD 16 to operate in the MRI mode for a period of time (e.g., 30 minutes, 1 hour, 2 hours, etc.), after which image disturbance instructions 78 may cause IMD 16 to operate in the normal mode. In some examples, in the MRI mode, the electronics used for stimulation, such as stimulation generator 64, could be, e.g., switched or electrically decoupled or be made immune (i.e., made not sensitive) to protect from malfunction cause by magnetic fields, e.g., caused by MRI induced EMI or the like. For instance, electronic path-ways within IMD 16 may be switched and/or decoupled such that induced currents will not flow directly into the electronics, but for example over the casing/grounds of IMD 16. As discussed above, when operating in the MRI mode, image disturbance instructions 78, as executed by processor 60, may not cause one or more components of IMD 16 to disturb images patient 12 generated by an MRI scanner.

Figure 3:
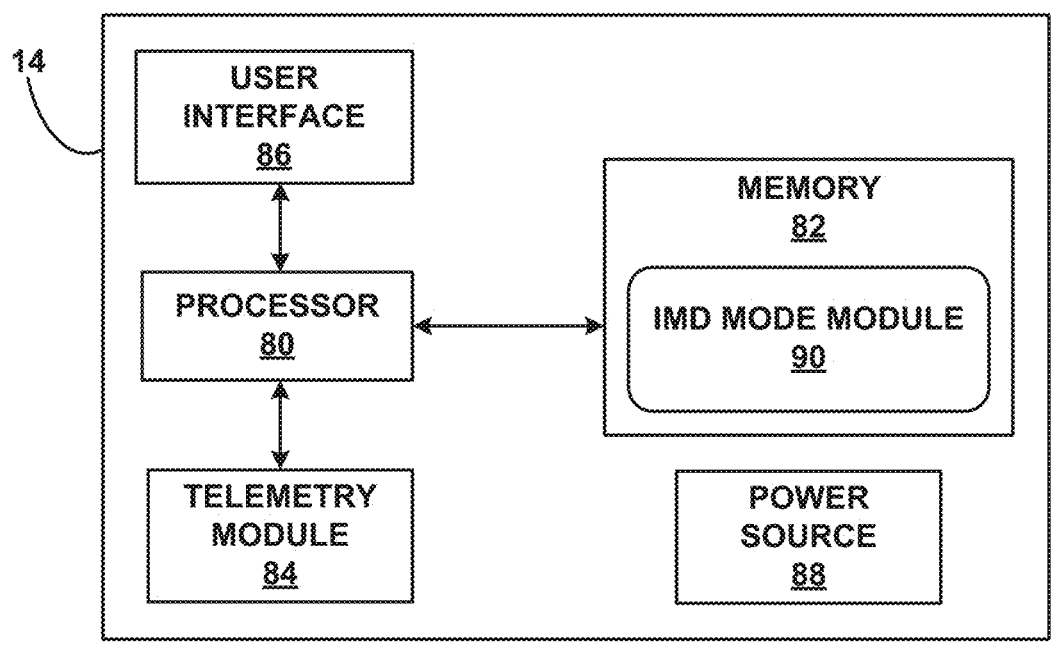
FIG. 3 is a functional block diagram illustrating components of an example medical device programmer configured to program an IMD, in accordance with one or more techniques of the disclosure.

FIG. 3 is a functional block diagram illustrating components of an example medical device programmer 14 (FIG. 1). Programmer 14 includes processor 80, memory 82, telemetry module 84, user interface 86, and power source 88. Processor 80 controls user interface 86 and telemetry module 84, and stores and retrieves information and instructions to and from memory 82. Programmer 14 may be configured for use as a clinician programmer or a patient programmer. Processor 80 may comprise any combination of one or more processors including one or more microprocessors, DSPs, ASICs, FPGAs, or other equivalent integrated or discrete logic circuitry. Accordingly, processor 80 may include any suitable structure, whether in hardware, software, firmware, or any combination thereof, to perform the functions ascribed herein to processor 80.

A user, such as a clinician or patient 12, may interact with programmer 14 through user interface 86. User interface 86 includes a display (not shown), such as a LCD or LED display or other type of screen, with which processor 80 may present information related to the therapy (e.g., electrodes and associated therapeutic windows). In addition, user interface 86 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processor 80 of programmer 14 and provide input. In other examples, user interface 86 also includes audio circuitry for providing audible notifications, instructions or other sounds to patient 12, receiving voice commands from patient 12, or both.

Memory 82 may include instructions for operating user interface 86 and telemetry module 84, and for managing power source 88. In the example shown in FIG. 3, memory 82 also stores IMD mode module 90.

As discussed in further detail below and in accordance with one or more techniques of this disclosure, in some examples, memory 62 may store IMD mode module 90, which may include instructions that are executable by processor 80 to output a request for an IMD to operate in an MRI mode in which the IMD does not disturb an image, such as an image generated by an MRI scanner. For instance, when patient 12 is to undergo an MRI procedure, programmer 14 may transmit a request for IMD 16 to operate in the MRI mode (e.g., so that clear, undisturbed images of patient 12 may be generated by the MRI scanner).

In some examples, patient 12, a clinician or another user may interact with user interface 86 of programmer 14 in other ways to manually select therapy programs, generate new therapy programs, modify therapy programs, transmit the new programs to IMD 16, or any combination thereof.

Memory 82 may include any volatile or nonvolatile memory, such as RAM, ROM, EEPROM or flash memory. Memory 82 may also include a removable memory portion that may be used to provide memory updates or increases in memory capacities. A removable memory may also allow sensitive patient data to be removed before programmer 14 is used by a different patient.

Wireless telemetry in programmer 14 may be accomplished by RF communication or proximal inductive interaction of external programmer 14 with IMD 16. This wireless communication is possible through the use of telemetry module 84. Accordingly, telemetry module 84 may be similar to the telemetry module contained within IMD 16. In other examples, programmer 14 may be capable of infrared communication or direct communication through a wired connection. In this manner, other external devices may be capable of communicating with programmer 14 without needing to establish a secure wireless connection.

Power source 88 is configured to deliver operating power to the components of programmer 14. Power source 88 may include a battery and a power generation circuit to produce the operating power. In some examples, the battery may be rechargeable to allow extended operation. Recharging may be accomplished by electrically coupling power source 88 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to operate.

While various information is illustrated and described as stored in memory 82 of programmer 14, it will be understood that some or all of this information could alternatively or additionally be stored within memory 62 of IMD 16. Moreover, at least some of the functionality ascribed to processor 80 of programmer 14 may instead or additionally be ascribed to processor 60 of IMD as discussed below (and vice versa).

Figure 4:
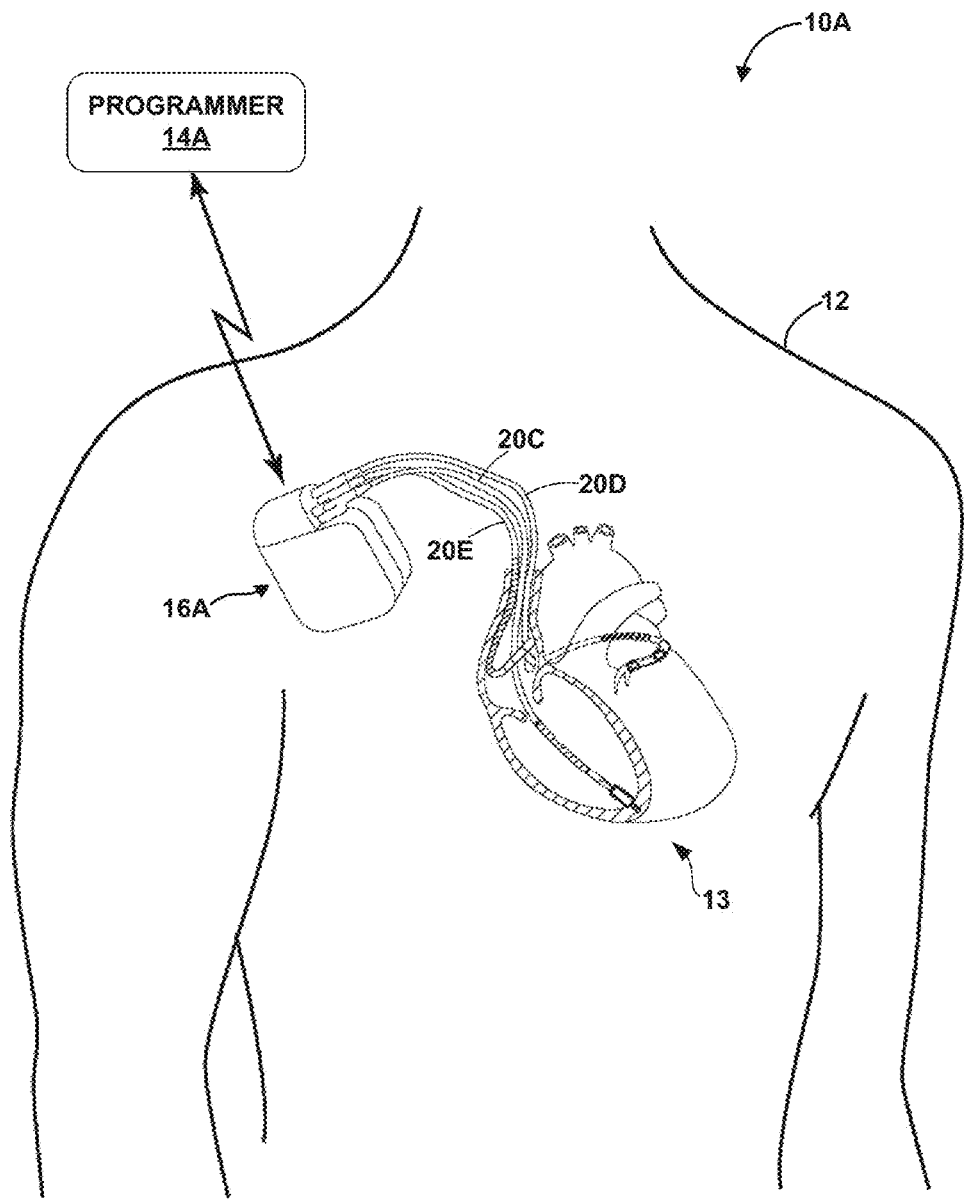
FIG. 4 is a conceptual diagram illustrating an example therapy system that may be used for sensing of physiological parameters of a patient and/or to provide therapy to a heart of the patient, in accordance with one or more techniques of the disclosure.

FIG. 4 is a conceptual diagram illustrating an example therapy system 10A that may be used for sensing of physiological parameters of patient 12 and/or to provide therapy to heart 13 of patient 12, in accordance with one or more techniques of this disclosure. System 10A includes IMD 16A, which is coupled to leads 20C-20E, and programmer 14A. IMD 16A may be, for example, an implantable pacemaker, cardioverter, and/or defibrillator, or a combined pacemaker and cardioverter-defibrillator, that provides electrical stimulation to heart 13 via electrodes coupled to one or more of leads 20C-20E.

In addition providing electrical stimulation to heart 13, IMD 16A may be configured to perform techniques similar to IMD 16 of FIGS. 1 and 2. For instance, IMD 16A may be configured to disturb an image of patient 12 generated by an MRI scanner. In some examples, IMD 16A may disturb the image of patient 12 in accordance with the techniques discussed below with reference to FIG. 5 and/or FIG. 6. For example, IMD 16A may include one or more components, such as a stimulation generator and/or a telemetry module, configured to generate a disturbing RF electromagnetic field.

Figure 5:
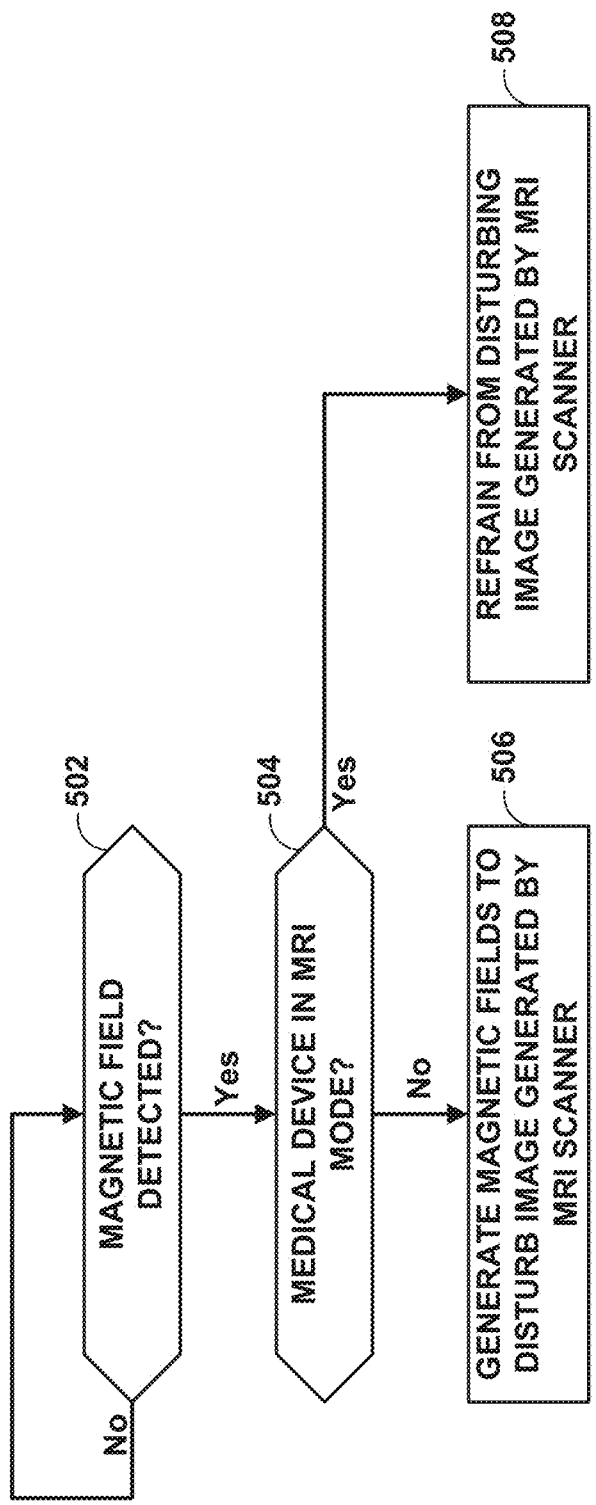
FIG. 5 is a flow diagram of an example technique for disturbing an image generated by an MRI scanner, in accordance with one or more techniques of the disclosure.

FIG. 5 is a flow diagram of an example technique for disturbing an image generated by an MRI scanner, in accordance with one or more techniques of this disclosure. For purposes of illustration, the technique of FIG. 5 is primarily described as being performed by IMD 16 of FIGS. 1 and 2, however in other examples, other IMDs may perform any portion of the technique of FIG. 5. For example, IMD 16A of FIG. 4 may perform the technique of FIG. 5.

As illustrated in FIG. 5, IMD 16 may determine whether a magnetic field is detected (502). For instance, processor 60 may determine whether a magnetic field is detected based on a signal received from magnetic field detector 79. In some examples, processor 60 may determine that a magnetic field is present if the signal received from magnetic field detector 79 indicates that a high-intensity magnetic field, such as the magnetic field generated by an MRI scanner, is present. If a magnetic field is not detected ("No" branch of 502), IMD 16 may continue to determine whether a magnetic field is detected (502).

If a magnetic field is detected ("Yes" branch of 502), IMD 16 may determine whether it is operating in an MRI mode (504). As discussed above, when patient 12 is to undergo an MRI procedure, image disturbance instructions 78 may be executable by processor 60 to operate in the MRI mode. If IMD 16 is operating in the MRI mode ("Yes" branch of 504), IMD 16 may refrain from disturbing images generated by an MRI scanner (508). In some examples, IMD 16 may operate in the MRI mode for a period of time, after which IMD 16 may return to operation in the stimulation mode and/or the disturb mode. In this way, IMD 16 may enable the MRI scanner to generate un-disturbed images of patient 12.

If IMD 16 is not operating in the MRI mode ("No" branch of 504), IMD 16 may generate one or more magnetic fields to disturb images generated by the MRI scanner (506). For instance, as discussed above, image disturbance instructions 78 may be executable by processor 60 to cause stimulation generator 64 of IMD 16 to generate low frequency magnetic fields (e.g., in a range of 0 Hertz to 5000 Hertz) and/or cause telemetry module 70 of IMD 16 to generate RF electromagnetic fields (e.g., in a range of 30 Mega-Hertz to 5000 Mega-Hertz). As discussed above, by generating low frequency magnetic fields, stimulation generator 64 may distort the local magnetic field gradients used by the MRI scanner for image localization, and by generating RF electromagnetic fields, telemetry module 70 may distort the MRI scanner's read-out of the Larmor resonance frequencies of i.e., protons, which may lead to a large image intensity change. In this way, IMD 16 may disturb images of patient 12 generated by an MRI scanner.

An operator of the MRI scanner may notice that the generated images are disturbed and perform one or more actions to avoid damaging the medical device and/or injuring the patient. For instance, the operator of the MRI scanner may notice that the generated images are disturbed in a manner similar to the images of FIGS. 10A-10C. Typically, the MRI scanner may make quick survey scans (only lasting for a couple of seconds) prior to real scanning, to determine the Field of View or Region of Interest for positioning, landmarks identification, or the like. These survey scans may result in some heating (e.g., of IMD 16). However the heating rates and response times are on the order of minutes. As the techniques of this disclosure may disturb the survey scan images, the operator of the MRI scanner may detect IMD 16 faster (i.e., less than the order of minutes), which may be before significant heating may occur.

In some examples, an image processor coupled to the MRI scanner may process the images generated by the MRI scanner to determine whether the images are disturbed. In response to determining that the images are disturbed, the image processor may output one or more alerts to notify the operator of the MRI scanner that patient 12 may have an IMD.

Figure 6:
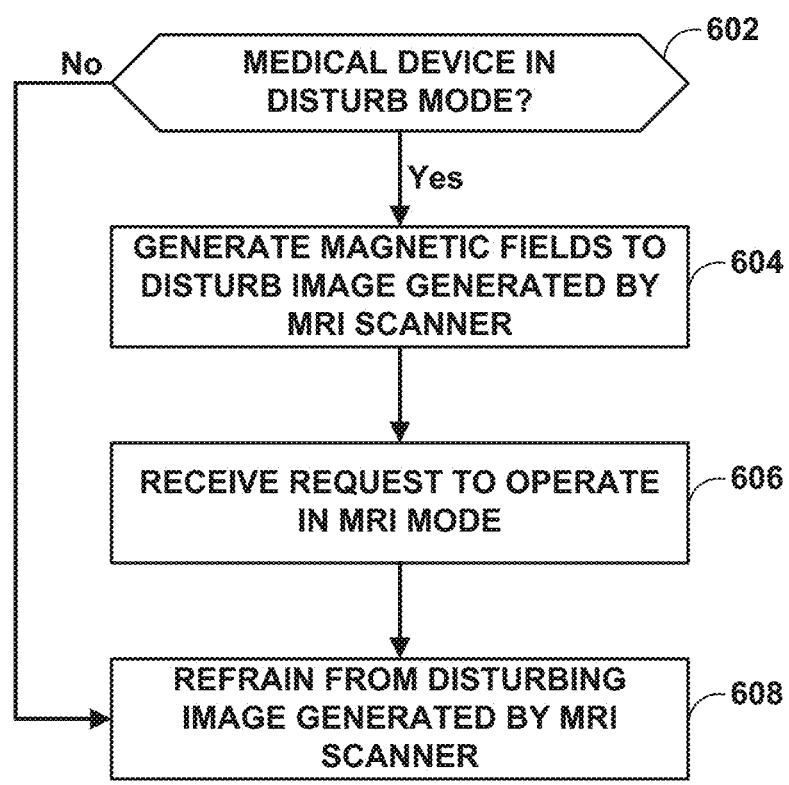
FIG. 6 is a flow diagram of another example technique for disturbing an image generated by an MRI scanner, in accordance with one or more techniques of the disclosure.

FIG. 6 is a flow diagram of another example technique for disturbing an image generated by an MRI scanner, in accordance with one or more techniques of this disclosure. For purposes of illustration, the technique of FIG. 6 is primarily described as being performed by IMD 16 of FIGS. 1 and 2; however, in other examples, other IMDs may perform any portion of the technique of FIG. 6. For example, IMD 16A of FIG. 4 may perform the technique of FIG. 6.

As illustrated in FIG. 6, IMD 16 may determine whether IMD 16 is operating in a disturb mode (602). In the example of FIG. 6, IMD 16 may operate in the disturb mode when not operating in the MRI mode. Alternatively (as discussed above in the example of FIG. 5), IMD 16 may operate in the disturb mode in response to detecting a magnetic field, such as a magnetic field generated by an MRI scanner.

If IMD 16 is not operating in the disturb mode ("No" branch of 602), IMD 16 may refrain from disturbing images generated by an MRI scanner (608). For instance, IMD 16 may operate in one or both of a stimulation mode or an MRI mode. In this way, IMD 16 may enable the MRI scanner to generate un-disturbed images of patient 12.

If IMD 16 is operating in the disturb mode ("Yes" branch of 602), IMD 16 may generate one or more magnetic fields to disturb images generated by the MRI scanner (604). For instance, IMD 16 may generate one or more magnetic fields to disturb images generated by the MRI scanner as described above with reference to box 506 of FIG. 5. In this way, IMD 16 may disturb images of patient 12 generated by an MRI scanner.

IMD 16 may receive a request to operate in an MRI mode (606). For instance, when patient 12 is to undergo an MRI procedure, an external device, such as programmer 14, may transmit a request for IMD 16 to operate in an MRI mode. In response to receiving the request to operate in the MRI mode, IMD 16 may refrain from disturbing images generated by an MRI scanner (608).

Figure 7:
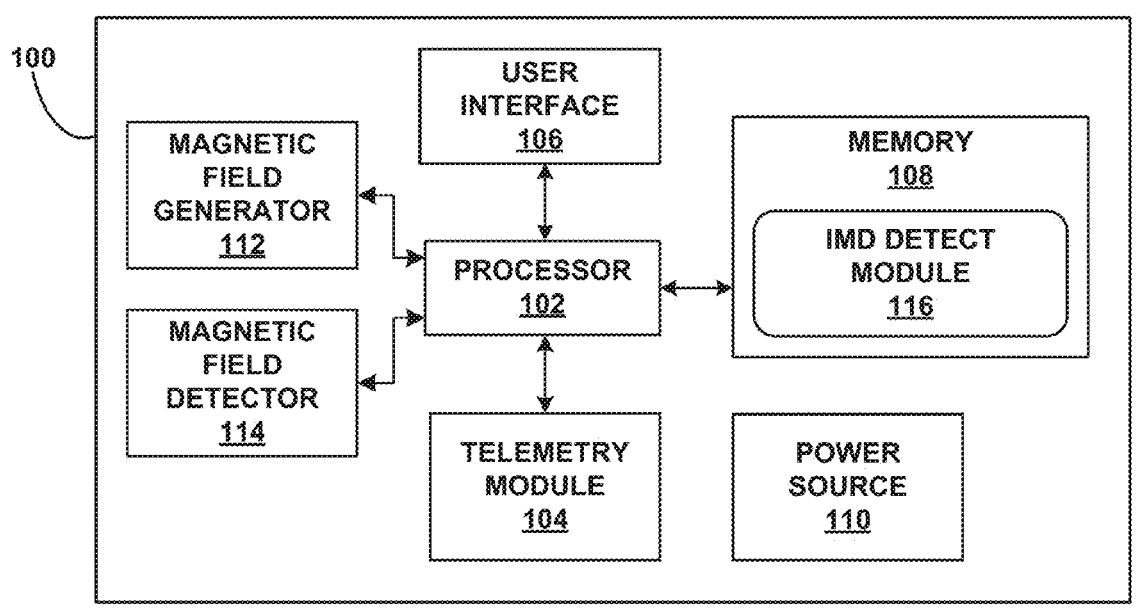
FIG. 7 is a functional block diagram illustrating components of an example medical device detector, in accordance with one or more techniques of the disclosure.

FIG. 7 is a functional block diagram illustrating components of an example medical device detector 100, in accordance with one or more techniques of this disclosure. As illustrated in FIG. 7, medical device detector 100 includes processor 102, telemetry module 104, user interface 106, memory 108, power source 110, magnetic field generator 112, and magnetic field detector 114. In some examples, medical device detector 100 may be used in a clinic, hospital, fixed or mobile imaging suite or any other setting where MRI scanners are used to scan patients.

Processor 102 controls user interface 106, telemetry module 104, magnetic field generator 112, and magnetic field detector 114, and stores and retrieves information and instructions to and from memory 108. Processor 102 may comprise any combination of one or more processors including one or more microprocessors, DSPs, ASICs, FPGAs, or other equivalent integrated or discrete logic circuitry. Accordingly, processor 102 may include any suitable structure, whether in hardware, software, firmware, or any combination thereof, to perform the functions ascribed herein to processor 102.

A user, such as a clinician or patient 12, may interact with medical device detector 100 through user interface 106. User interface 106 includes a display (not shown), such as a LCD or LED display or other type of screen, with which processor 102 may present information related to the detection and/or control of a medical device. In addition, user interface 106 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processor 102 of medical device detector 100 and provide input. In other examples, user interface 106 also includes audio circuitry for providing audible notifications, instructions or other sounds to the user, receiving voice commands from the user, or both.

Memory 108 may include instructions for operating user interface 106 and telemetry module 104, and for managing power source 110. In the example shown in FIG. 7, memory 108 also stores IMD detect module 116.

Magnetic field generator 112 may generate one or more magnetic fields. For instance, magnetic field generator 112 may be controllable by processor 102 to generate one or more magnetic fields to simulate the magnetic fields generated by an MRI scanner, such as a strong magnetic field.

Magnetic field detector 114 may detect the presence and/or intensity of a magnetic field. For instance, magnetic field detector 114 may detect the presence of one or more magnetic fields generated by an IMD attempting to disturb images generated by an MRI scanner. Magnetic field detector 114 may provide an output indicating the intensities and/or frequencies of the one or more magnetic fields to one or more components of medical device detector 100, such as processor 102.

Memory 108 may include any volatile or nonvolatile memory, such as RAM, ROM, EEPROM or flash memory. Memory 108 may also include a removable memory portion that may be used to provide memory updates or increases in memory capacities. A removable memory may also allow sensitive patient data to be removed before medical device detector 100 is used with a different patient.

Wireless telemetry in medical device detector 100 may be accomplished by RF communication or proximal inductive interaction of medical device detector 100 with IMD 16. This wireless communication is possible through the use of telemetry module 104. Accordingly, telemetry module 104 may be similar to the telemetry module contained within IMD 16. In other examples, medical device detector 100 may be capable of infrared communication or direct communication through a wired connection. In this manner, other external devices may be capable of communicating with medical device detector 100 without needing to establish a secure wireless connection.

Power source 110 is configured to deliver operating power to the components of medical device detector 100. Power source 110 may include a battery and a power generation circuit to produce the operating power. In some examples, the battery may be rechargeable to allow extended operation. Recharging may be accomplished by electrically coupling power source 110 to a cradle or plug that is connected to an alternating current (AC) outlet. In addition, recharging may be accomplished through proximal inductive interaction between an external charger and an inductive charging coil within medical device detector 100. In other examples, traditional batteries (e.g., nickel cadmium or lithium ion batteries) may be used. In addition, medical device detector 100 may be directly coupled to an alternating current outlet to operate.

As discussed above, devices other than MRI scanners may be used to detect the presence/existence of an IMD. In accordance with one or more techniques of this disclosure, medical device detector 100 may be used to detect the presence/existence of an IMD. For instance, where medical device detector 100 is a hand-held device, patient 12 may be scanned with medical device detector 100 prior to entering an MRI scanner.

As illustrated in FIG. 7, memory 108 may store IMD detect module 116, which may include instructions that are executable by processor 102 to detect the presence/existence of an IMD. When executed by processor 102, IMD detect module 116 may cause one or more components of medical device detector 100 to determine that an IMD is attempting to disturb images generated by MRI scanners. For instance, IMD detect module 116 may analyze aspects of one or more magnetic fields detected by magnetic field detector 114. If IMD detect module 116 determines that the aspects of the one or more magnetic fields are consistent with magnetic fields generated by an IMD attempting to disturb images generated by MRI scanners, IMD detect module 116 may determine that an IMD is present.

In some examples, such as where medical device detector 100 is used to detect IMDs that selectively attempt to disturb images generated by MRI scanners, IMD detect module 116 may cause one or more components of medical device detector 100 to "trigger" IMDs into attempting to disturb images generated by MRI scanners. For instance, IMD detect module 116 may cause one or more components of medical device detector 100 to emit a query signal, which may be received and detected by an IMD, such as IMD 16, if present. As one example, IMD detect module 116 may cause magnetic field generator 112 to generate one or more magnetic fields to simulate the magnetic fields generated by an MRI scanner, such as a strong magnetic field. As discussed above, in some examples, the presence of such magnetic fields may cause an IMD, such as IMD 16, to attempt to disturb images generated by MRI scanners.

In response to determining that an IMD is present, processor 102, by execution of IMD detect module 116, may cause one or more components of medical device detector 100 to alert the user of medical device detector 100 to the presence of the IMD. For instance, IMD detect module 116 may cause user interface 106 to output one or more visual, audio, or haptic alerts. In this way, the user of medical device detector 100 may be alerted to the presence of an IMD.

In some examples, IMD detect module 116, as executed by processor 102, may output one or more signals to temporarily prevent activation of an MRI scanner in response to determining that an IMD is present. In this way, medical device detector 100 may function as a safety interlock device for an MRI scanner.

In some examples, even though an IMD is present, an MRI imaging procedure may still be conducted. For instance, where the IMD is an MRI conditional IMD, the patient may still be scanned within certain limits. In some examples, in order to scan a patient with an IMD that attempts to disturb images generated by MRI scanners, the IMD may be placed into an MRI mode in which the IMD does not emit a disturbing field.

In accordance with one or more techniques of this disclosure, medical device detector 100 may be configured to cause an IMD to operate in an MRI mode. For instance, medical device detector 100 may output a request for an IMD to operate in an MRI mode in which the IMD does not disturb images generated by MRI scanners. For instance, when patient 12 is to undergo an MRI procedure, telemetry module 104 may transmit a request for IMD 16 to operate in the MRI mode (e.g., so clear images of patient 12 may be generated by an MRI scanner). In some examples, once the IMD is in the MRI mode, medical device detector 100 may output an OK signal to the user of medical device detector 100 (e.g., via user interface 106).

Figure 8:
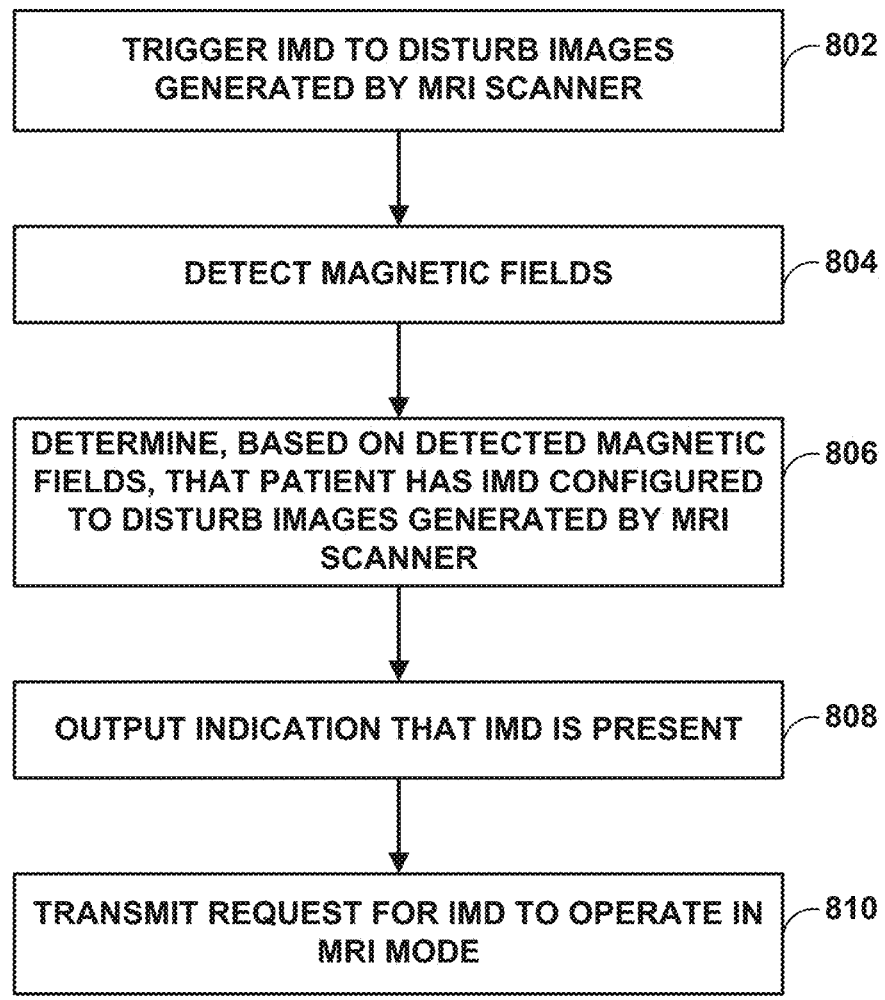
FIG. 8 is a flow diagram of an example technique for detecting an IMD configured to disturb images generated by an MRI scanner, in accordance with one or more techniques of the disclosure.

FIG. 8 is a flow diagram of an example technique for detecting an IMD configured to disturb images generated by an MRI scanner, in accordance with one or more techniques of this disclosure. For purposes of illustration, the technique of FIG. 8 is primarily described as being performed by medical device detector 100 of FIG. 7. However, in other examples, other devices may perform any portion of the technique of FIG. 8. For example, programmer 14 of FIG. 3 or programmer 14A of FIG. 4, which may be a patient or clinician programmer, may perform the technique of FIG. 8.

In practice, medical device detector 100 may be used to determine whether a patient has an IMD configured to disturb images generated by an MRI scanner. As illustrated in FIG. 8, medical device detector 100 may trigger an IMD to disturb images generated by an MRI scanner (802). For instance, processor 102 may execute IMD detect module 116 to cause one or more components of medical device detector 100 to emit a query signal, which may be received and detected by an IMD, such as IMD 16, if present. As one example, IMD detect module 116 may cause magnetic field generator 112 to generate one or more magnetic fields to simulate the magnetic fields generated by an MRI scanner, such as a strong magnetic field. As discussed above, in some examples, the presence of such magnetic fields may cause an IMD, such as IMD 16, to attempt to disturb images generated by MRI scanners.

Medical device detector 100 may detect magnetic fields (804). For instance, magnetic field detector 114 may detect the presence of one or more magnetic fields generated by an IMD attempting to disturb images generated by an MRI scanner. Magnetic field detector 114 may output an indication of the detected magnetic fields to processor 102.

Medical device detector 100 may determine, based on the detected magnetic fields, that the patient has an IMD configured to disturb images generated by an MRI scanner (806). For instance, processor 102 may execute IMD detect module 116 to analyze aspects (e.g., frequencies, periods, duty cycles) of one or more magnetic fields detected by magnetic field detector 114. If IMD detect module 116 determines that the aspects of the one or more magnetic fields are consistent with magnetic fields generated by an IMD attempting to disturb images generated by MRI scanners, IMD detect module 116 may determine that such an IMD is present.

Medical device detector 100 may output an indication that the IMD is present (808). For instance, processor 102 may cause one or more components of medical device detector 100 to alert the user of medical device detector 100 to the presence of the IMD. For instance, processor 102 may cause user interface 106 to output one or more visual, audio, or haptic alerts. In this way, the user of medical device detector 100 may be alerted to the presence of an IMD.

As discussed above and in some examples, even though an IMD is present, an MRI may still be conducted. For instance, where the IMD is an MRI conditional IMD the patent may still be scanned within certain limits. In some examples, in order to scan a patient with an IMD that attempts to disturb images generated by MRI scanners, the IMD may be placed into an MRI mode in which the IMD does not disturb images generated by MRI scanners.

Medical device detector 100 may transmit a request for the IMD to operate in the MRI mode (810). For instance, processor 102 may cause telemetry module 104 to transmit a request for IMD 16 to operate in the MRI mode (e.g., so clear images of patient 12 may be generated by an MRI scanner). In some examples, once IMD 16 is in the MRI mode, medical device detector 100 may output an OK signal to the user of medical device detector 100 (e.g., via user interface 106). For instance, medical device detector 100 may output an OK signal in response to receiving an acknowledgement from IMD 16 that IMD 16 is operating in the MRI mode.

Figure 9:
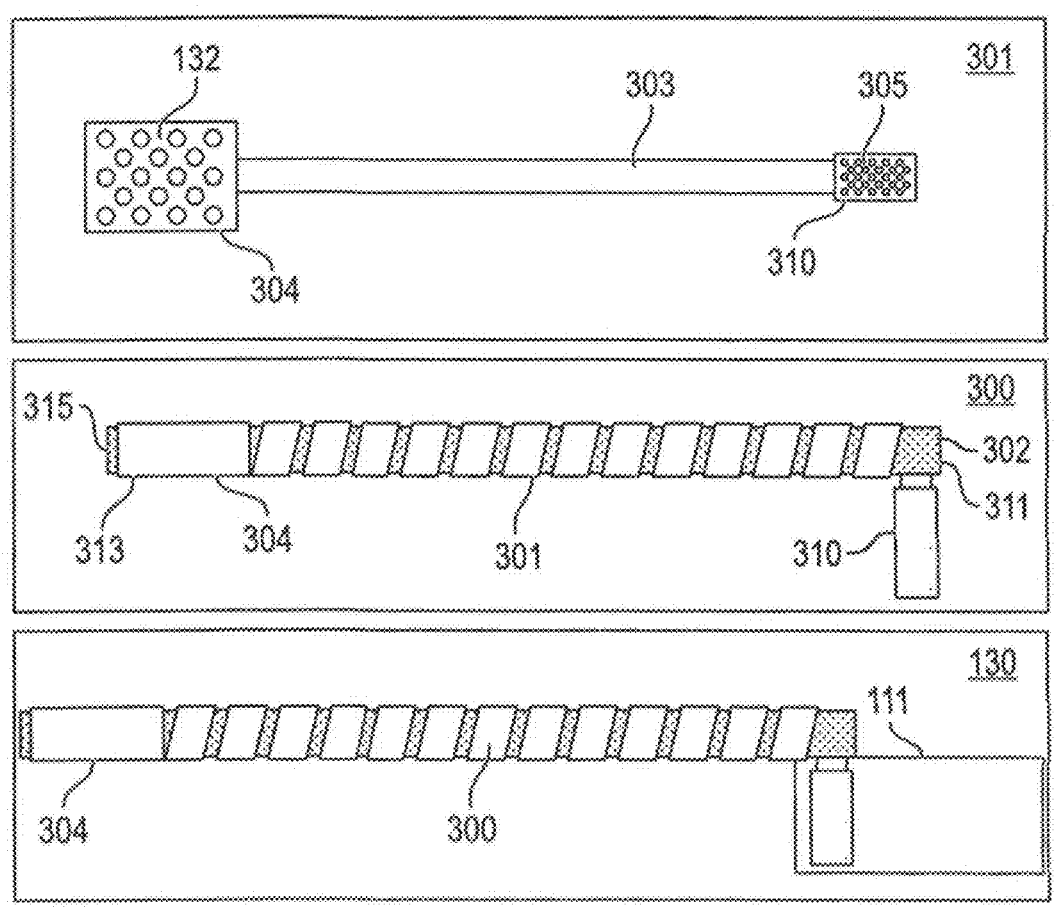
FIG. 9 illustrates an example architecture for a deep brain stimulation (DBS) probe, in accordance with one or more techniques of the disclosure.

FIG. 9 illustrates an example architecture for a DBS lead, in accordance with one or more techniques of this disclosure. In some examples, the DBS lead 300 shown in FIG. 9 may be an example combination of one or more of lead extension 18, leads 20, electrodes 24, electrodes 26 of FIG. 1. As illustrated in FIG. 9, DBS probe 130 include DBS lead 300 and active lead can 111, which may include electronic means to address electrodes 132 on distal end 304 of thin film 301, which may be arranged at distal end 313 and next to distal tip 315 of DBS lead 300. The lead 300 may include a carrier 302 for a thin film 301, said carrier 302 providing the mechanical configuration of the DBS lead 300 and the thin film 301. The thin film 301 may include at least one electrically conductive layer, preferably made of a biocompatible material.

The thin film 301 is assembled to the carrier 302 and further processed to constitute the lead 300. The thin film 301 for a lead is preferably formed by a thin film product having a distal end 304, a cable 303 with metal tracks and a proximal end 310. The proximal end 310 of the thin film 301 arranged at the proximal end 311 of the lead 300 is electrically connected to the active lead can 111. The active lead can 111 comprises the switch matrix of the DBS steering electronics. The distal end 304 comprises the electrodes 132 for the brain stimulation. The proximal end 310 comprises the interconnect contacts 305 for each metal line in the cable 303. The cable 303 comprises metal lines (not shown) to connect each distal electrodes 132 to a designated proximal contact 305.

In some examples, the active lead can 111 may comprise a stimulation generator. The stimulation generator of active lead can 111 may be provided instead of, or in addition to, a stimulation generator provided by the IMD, such as stimulation generator 64 of IMD 16 (FIG. 2). In some examples, a stimulation generator of active lead can 111 may operate in any of the ways described herein to provide stimulation signals to electrodes 132 of lead and/or to generate signals that disturb an MRI image. In such cases, the stimulation generator of active lead can 111 may be controlled to enter any of the modes described herein based on signals received wirelessly from an external device (e.g., programmer 14, medical device detector 100), based on signals received from an IMD to which lead 300 is electrically and mechanically coupled, and/or based on controls generated by circuitry residing within active lead can 111, such as circuitry to detect a magnetic field.

Figure 10A:
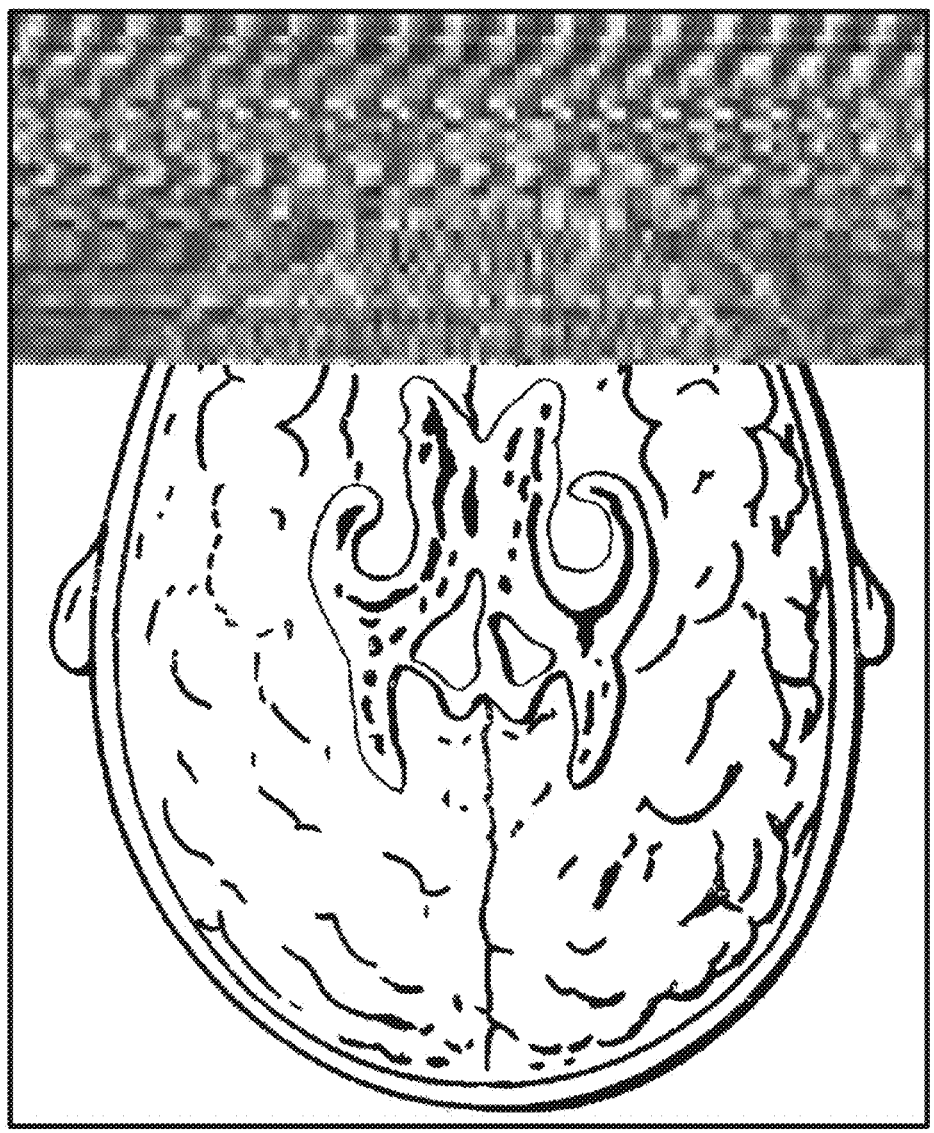
FIGS. 10A-10C illustrate examples of images generated by an MRI scanner that have been disturbed by an IMD, in accordance with one or more techniques of the disclosure.
Figure 10B:
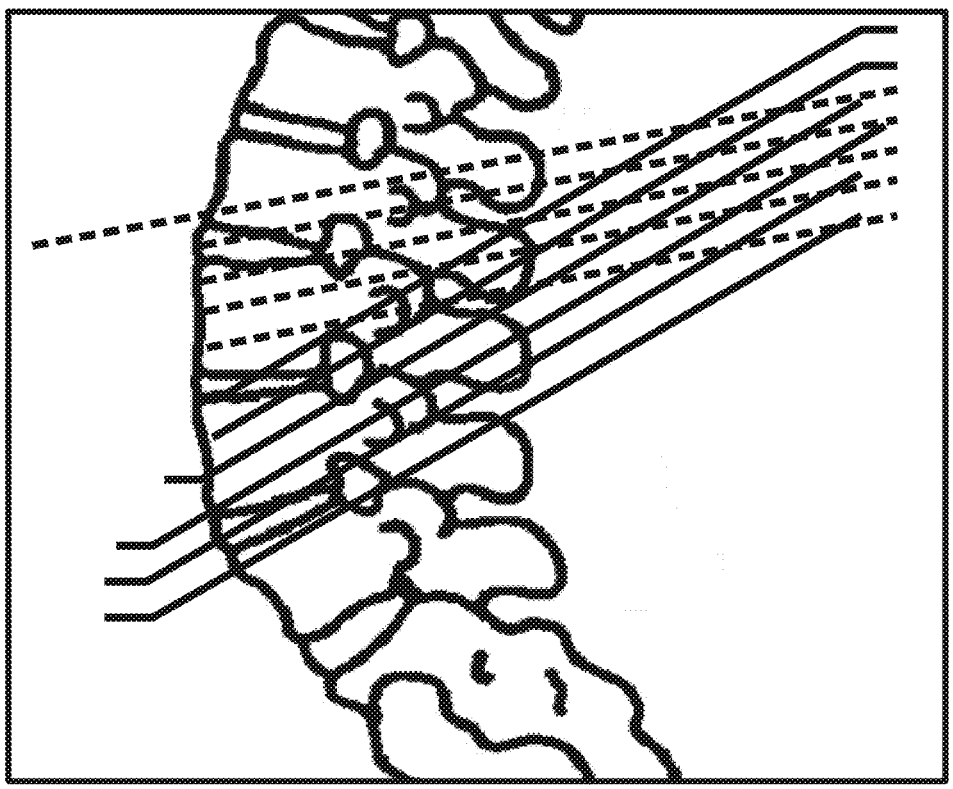
Figure 10C:
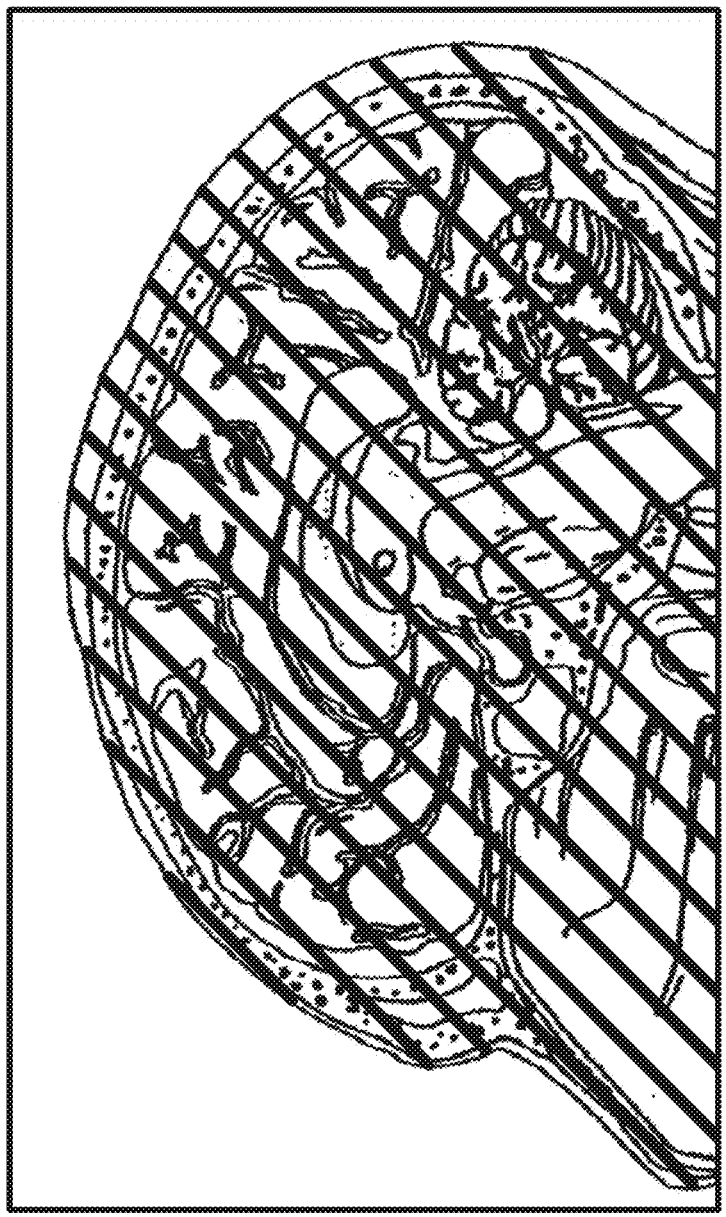

FIGS. 10A-10C illustrate examples of images generated by an MRI scanner that have been disturbed by an IMD, in accordance with one or more techniques of the disclosure. FIG. 10A illustrates a transverse MR image of the brain. FIG. 10B illustrates a sagittal MR image of the spinal cord (lumbar). FIG. 10C illustrates a sagittal MR image of the brain. As discussed above, an IMD, such as IMD 16, may disturb images generated by an MRI scanner. As shown in each of FIGS. 10A-10C, as a result of the disturbance, the generated images may include one or more artifacts. For instance, the image of FIG. 10A includes a zipper artifact in the form of a distortion across the top third of the image, the image of FIG. 10B includes a slice-overlap artifact (also known as a cross-talk artifact), and the image of FIG. 10C includes a zipper artifact in the form of diagonal lines.

The following numbered clauses may illustrate one or more aspects of the disclosure and such aspects may be combined in any manner and in any combination:

Clause 1. An active implantable medical device, for example an active implantable medical system for stimulation and/or recording, comprising at least one MR disturbing means being adapted to disturb the generation of MR imaging.

Clause 2 The device of clause 1, wherein the active implantable medical system is an active implantable medical system for neurostimulation and/or neurorecording.

Clause 3. The device of clause 1 or 2, wherein the MR disturbing means (320) are adapted to create a disturb signal.

Clause 4. The device of clause 1, 2, or 3, wherein the MR disturbing means (320) comprise at least one low frequency magnetic field generating means.

Clause 5. The device of clause 4, wherein the at least one low frequency magnetic field generating means is adapted to generate a low frequency magnetic field in a range of approx. 0-5000 Hz.

Clause 6. The device of clause 4 or clause 5, wherein the at least one low frequency magnetic field generating means is or is provided by a stimulation pulse generator.

Clause 7. The device according to one of the preceding clauses, wherein the MR disturbing means comprise at least one radiofrequency electromagnetic field generating means.

Clause 8. The device of clause 7, wherein the at least one radiofrequency electromagnetic field generating means is adapted to generate a radiofrequency electromagnetic field in a range of approx. 30-5000 MHz.

Clause 9. The device of clause 7 or clause 8, wherein the at least one radiofrequency electromagnetic field generating means is or is provided by a wireless RF telemetry or inductive communication link.

Clause 10. The device according to one of the preceding clauses, wherein the device comprises detection means being adapted to detect a field or signal of an MRI apparatus.

Clause 11. The device according to one of the preceding clauses, wherein the device comprises a controller, which is adapted to switch the device from one mode into an MRI mode and vice versa.

Clause 12. The device according to clause 11, wherein the MRI mode is limited for a specific time limit and wherein after reaching the time limit the controller switches back to stimulation mode.

Clause 13. The device according to one of the preceding clauses, wherein MR disturbing means are adapted such that the MR disturbing means can be switched off.

Clause 14. The device according to one of the preceding clauses, wherein the MR disturbing means are adapted to send identification information, which can be identified by an MRI apparatus, especially wherein the identification information is an RF identification tag.

Clause 15. The device according to one of the preceding clauses, wherein the device is a system for deep brain stimulation.

Clause 16. A method of detecting an active implantable medical device, especially a system for neurostimulation and/or neurorecording, comprising at least the step of disturbing the generation of MR imaging by the device.

The term implantable medical device may cover both so-called active implants with powered means and passive implants with unpowered means, which are passively powered, e.g., by the MRI field. For example, even if such implants do not contain electronics to generate the disturbing signals, other means, such as passive (unpowered) transceivers could be used to receive MRI field signals (and energy) and send back, preferably modulated, disturb signals or distortion signals. The passively powered transceiver is powered entirely by the energy or stored energy derived from the MR, RF, or gradient fields provided by an MRI scanner.

The techniques described in this disclosure, including those attributed to IMD 16, programmer 14, medical device detector 100, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various examples have been described. These and other examples are within the scope of the following claims.

What is claimed is:

1. A method comprising:
generating, by one or more stimulation generators of a medical device implanted in a patient, electrical stimulation for delivery to the patient;
in response to detecting, by the medical device and while the medical device is operating in a disturb mode, magnetic fields generated by a magnetic resonance image (MRI) scanner, disturbing, by one or more components of the medical device, an image of the patient generated by the MRI scanner;
in response to receiving, by a telemetry module of the medical device and from an external device, a request for the medical device to operate in an MRI mode, refraining, by the medical device, from disturbing the image; and operating, by the medical device, in the disturb mode when not operating in the MRI mode.

2. The method of claim 1, wherein disturbing the image of the patient comprises generating, by a radio frequency (RF) transmitter of the telemetry module, RF electromagnetic fields.

3. The method of claim 1, wherein refraining, by the medical device, from disturbing the image comprises refraining from disturbing the image for a predetermined period of time.

4. An implantable medical device (IMD) comprising:
a telemetry module configured to communicate with an external device;
one or more stimulation generators configured to generate electrical stimulation for delivery to a patient;
a magnetic field detector configured to detect magnetic fields generated by a magnetic resonance image (MRI) scanner; and
one or more components configured to:
disturb, while the IMD is operating in a disturb mode and in response to the magnetic field detector detecting the magnetic fields generated by the MRI scanner, an image of the patient generated by the MRI scanner; and
not disturb the image while the IMD is operating in an MRI mode, wherein the IMD is configured to operate in the MRI mode in response to the telemetry module receiving a request for the IMD to operate in the MRI mode, and wherein the IMD is configured to operate in the disturb mode when not operating in the MRI mode.

5. The IMD of claim 4, wherein the one or more components include at least one of the one or more stimulation generators, and wherein the one or more stimulation generators are configured to generate low frequency magnetic fields to disturb the image of the patient.

6. The IMD of claim 5, wherein a frequency of the low frequency magnetic fields is in a range of 0-5000 Hz.

7. The IMD of claim 4, wherein the one or more components include a radio frequency (RF) transmitter of the telemetry module, and wherein the RF transmitter is configured to generate RF electromagnetic fields to disturb the image of the patient.

8. The IMD of claim 7, wherein a frequency of the RF electromagnetic fields is in a range of 30-5000 MHz.

9. The IMD of claim 6, wherein, in response to the telemetry module receiving the request for the IMD to operate in the MRI mode, the IMD is configured to operate in the MRI mode for a period of time after-which the IMD is configured to operate in the disturb mode.

10. The IMD of claim 6, wherein, to disturb the image, the one or more components are configured to cause one or more artifacts in the image of the patient generated by the MRI scanner.

11. A computer-readable storage medium storing instructions that, when executed, cause one or more processors of an implantable medical device (IMD) to:
cause one or more stimulation generators of the IMD to generate electrical stimulation for delivery to a patient;
in response to detecting, while the IMD is operating in a disturb mode, magnetic fields generated by a magnetic resonance image (MRI) scanner, cause one or more components of the IMD to disturb an image of the patient generated by the MRI scanner;
in response to receiving, via a telemetry module of the IMD and from an external device, a request for the IMD to operate in an MRI mode, refrain from causing the one or more components to disturb the image; and
operate in the disturb mode when not operating in the MRI mode.

12. The computer-readable storage medium of claim 11, wherein, to cause the one or more components to disturb the image of the patient, the instructions cause the one or more processors to cause a radio frequency (RF) transmitter of the telemetry module to generate RF electromagnetic fields.

13. The computer-readable storage medium of claim 11, further comprising instructions that cause the one or more processors to:
operate in the MRI mode for a period of time until operating in the disturb mode.

14. A medical device detector comprising:
a magnetic field detector;
a magnetic field generator;
a telemetry module configured to communicate with implantable medical devices (IMDs); and
one or more processors configured to:
cause the magnetic field generator to generate one or more magnetic fields to trigger IMDs to disturb images generated by a magnetic resonance image (MRI) scanner;
determine, based on one or more aspects of magnetic fields detected by the magnetic field detector, whether a patient has an implanted medical device (IMD) configured to disturb images generated by the MRI scanner;
output an indication when the IMD is present; and
cause the telemetry module to transmit, to the IMD of the patient, a request for the IMD to operate in an MRI mode in which the IMD refrains from disturbing images generated by the MRI scanner.

* * * * *